(12) United States Patent
De Oliveira et al.

(10) Patent No.: US 12,115,047 B2
(45) Date of Patent: *Oct. 15, 2024

(54) MENSTRUAL DEVICE AND APPLICATOR SYSTEM

(71) Applicant: Edgewell Personal Care Brands, LLC, Chesterfield, MO (US)

(72) Inventors: Ricardo De Oliveira, New Hope, PA (US); George Kormanos, Nashua, NH (US); Pankaj Nigam, Ridgewood, NJ (US); Hassan Mohamed, Bayonne, NJ (US); Richard Timmers, Saddle Brook, NJ (US); Rui Yang, Pompton Lakes, NJ (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/806,279

(22) Filed: Jun. 10, 2022

(65) Prior Publication Data

US 2022/0296432 A1 Sep. 22, 2022

Related U.S. Application Data

(63) Continuation of application No. 15/602,506, filed on May 23, 2017, now Pat. No. 11,389,337.

(Continued)

(51) Int. Cl.
*A61F 13/20* (2006.01)
*A61F 13/26* (2006.01)
(Continued)

(52) U.S. Cl.
CPC ...... *A61F 13/2045* (2013.01); *A61F 13/2028* (2013.01); *A61F 13/2037* (2013.01);
(Continued)

(58) Field of Classification Search
CPC ............... A61F 13/2045; A61F 13/20–2097
See application file for complete search history.

(56) References Cited

U.S. PATENT DOCUMENTS

| 1,263,797 A | 4/1918 | Norquist |
| 1,480,680 A | 1/1924 | Glover |

(Continued)

FOREIGN PATENT DOCUMENTS

| CA | 2137769 A1 | 5/1996 |
| CN | 101869515 A | 10/2010 |

(Continued)

OTHER PUBLICATIONS

"Test Data Radial Force Testing of Feminine Care Products, MED160071-D," Med Institute Incorporated, Jun. 3, 2016.

(Continued)

*Primary Examiner* — Susan S Su
*Assistant Examiner* — Meagan Ngo

(57) ABSTRACT

A menstrual device having a storage volume. The menstrual device has a frame and a fluid barrier seal layer attached to the exterior surface of the frame. The menstrual device has an expanded configuration that includes an at rest configuration and a deployed configuration. The menstrual device has a compact configuration where the menstrual device is confined to a size, shape and/or geometry smaller than an expanded configuration such that it can be more easily inserted into the body. The menstrual device in a compact configuration is contained within an applicator, where the applicator assists in ejecting the menstrual device into the body.

20 Claims, 22 Drawing Sheets

Related U.S. Application Data

(60) Provisional application No. 62/341,131, filed on May 25, 2016, provisional application No. 62/341,134, filed on May 25, 2016.

(51) Int. Cl.
  *A61F 13/28* (2006.01)
  *A61F 13/84* (2006.01)

(52) U.S. Cl.
  CPC ...... *A61F 13/2042* (2013.01); *A61F 13/2071* (2013.01); *A61F 13/28* (2013.01); *A61F 13/84* (2013.01); *A61F 13/2057* (2013.01); *A61F 13/2068* (2013.01); *A61F 13/266* (2013.01); *A61F 2013/8488* (2013.01)

(56) References Cited

U.S. PATENT DOCUMENTS

| | | |
|---|---|---|
| 1,555,708 A | 9/1925 | Gale |
| 1,634,555 A | 7/1927 | Peloubet |
| 1,669,295 A | 5/1928 | Hallenberg |
| 1,891,761 A | 12/1932 | Goddard |
| 1,996,242 A | 4/1935 | Hagerdom |
| 2,089,113 A | 8/1937 | Chalmers |
| 2,097,033 A | 10/1937 | McVitte |
| 2,141,026 A | 12/1938 | Valle |
| 2,330,257 A * | 9/1943 | Bailey ............. A61F 13/2037 604/377 |
| 2,534,900 A | 12/1950 | Chambers |
| 3,306,966 A | 2/1967 | Matejcek et al. |
| 3,404,682 A | 10/1968 | Waldron |
| 3,618,605 A | 11/1971 | Glassman |
| 3,626,942 A | 12/1971 | Tassette |
| 3,674,025 A | 7/1972 | Bleuer |
| 3,695,270 A | 10/1972 | Dostal |
| 3,712,305 A * | 1/1973 | Wennerblom ...... A61F 13/2051 604/385.18 |
| 3,749,024 A | 7/1973 | Pakulak, Jr. |
| 3,749,094 A | 7/1973 | Duncan |
| 3,811,445 A | 5/1974 | Dostal |
| 3,812,856 A | 5/1974 | Duncan et al. |
| 3,834,389 A | 9/1974 | Dulle |
| 3,845,766 A | 11/1974 | Zoller |
| 3,856,013 A | 12/1974 | Dulle |
| 4,018,225 A * | 4/1977 | Elmi ............... A61F 13/2037 604/377 |
| 4,274,412 A | 6/1981 | Austin |
| 4,374,522 A | 2/1983 | Olevsky |
| D323,212 S | 1/1992 | Crawford |
| 5,105,827 A | 4/1992 | Augros |
| 5,618,256 A | 4/1997 | Reimer |
| 5,743,893 A | 4/1998 | Kalb |
| 5,817,077 A | 10/1998 | Foley |
| 6,183,436 B1 | 2/2001 | Korteweg |
| 6,739,340 B1 | 5/2004 | Jensen |
| 6,743,212 B1 | 6/2004 | Cole et al. |
| 6,814,722 B2 | 11/2004 | Jackson et al. |
| 7,678,095 B2 | 3/2010 | Jackson et al. |
| 7,815,594 B2 | 10/2010 | Dougherty, Jr. et al. |
| 7,867,209 B2 | 1/2011 | Jorgensen et al. |
| 8,070,710 B2 | 12/2011 | Dougherty, Jr. |
| 8,696,957 B2 | 4/2014 | Dougherty, Jr. et al. |
| 9,192,522 B2 | 11/2015 | Edgett et al. |
| 2002/0010443 A1 | 1/2002 | Zadini et al. |
| 2008/0287902 A1 | 11/2008 | Edgett et al. |
| 2010/0198133 A1 | 8/2010 | Dougherty, Jr. et al. |
| 2010/0268182 A1 | 10/2010 | Edgett et al. |
| 2010/0312204 A1 | 12/2010 | Sheu |
| 2011/0160526 A1* | 6/2011 | Zunker ............. A61F 13/266 600/29 |
| 2012/0101467 A1* | 4/2012 | Watanabe ........... A61F 13/2071 28/118 |
| 2012/0165599 A1 | 6/2012 | Ellefson et al. |
| 2012/0165601 A1 | 6/2012 | Ellefson et al. |
| 2014/0012221 A1* | 1/2014 | Henson ............. A61F 13/2034 604/385.17 |
| 2014/0039342 A1* | 2/2014 | Edmunds ............ A61F 13/34 604/385.18 |
| 2014/0041817 A1* | 2/2014 | Sealey .............. D21H 21/22 162/13 |
| 2014/0115844 A1* | 5/2014 | Wolter ............. A61F 13/2077 28/118 |
| 2014/0188064 A1 | 7/2014 | Yamaki |
| 2015/0006121 A1 | 7/2015 | Ramachandran et al. |
| 2016/0158070 A1 | 6/2016 | Acton et al. |

FOREIGN PATENT DOCUMENTS

| | | |
|---|---|---|
| CN | 102429759 A | 5/2012 |
| DE | 2324264 A1 | 11/1973 |
| FR | 761699 A | 3/1934 |
| GB | 538164 A | 7/1941 |
| GB | 2502807 A | 12/2013 |
| JP | S49-055196 A | 5/1974 |
| JP | S49-084095 A | 8/1974 |
| WO | 2010120619 A1 | 10/2010 |
| WO | 2013182835 A1 | 12/2013 |

OTHER PUBLICATIONS

"Test Data Radial Force Testing of Feminine Care Products, MED160112-D," Med Institute Incorporated, Oct. 6, 2016.

"Comparison Between Measurements Obtained With Three Different Perineometers," Clinics 2009;64(6):527-33; Patricia Brentegani Barbosa, Maira Menezes Franco, Flaviane de Oliveira Souza, Flavia Ignacio Antonio, Thais Montezuma, Cristine Homsi Jorge Ferreira.

Search Report and Written Opinion issued in connection with corresponding PCT Application No. PCT/US2017/003967 dated Jul. 19, 2017.

Unofficial translation of Chinese Office Action and Search Report issued in connection with corresponding Chinese Application No. 201780046627.2 dated Dec. 3, 2020.

Unofficial translation of Japanese Office Action issued in connection with JP Application No. 2018-561485 dated Apr. 22, 2021.

The European Search Report and Opinion issued in connection with EP Application 22185652.9 dated Oct. 19, 2022.

Unofficial translation of Mexican Office Action issued in connection with MX Application No. MX/a/2018/014440 dated Oct. 6, 2022.

Examination Report issued in Canadian Patent Application No. 3,025,167 on Dec. 5, 2023.

\* cited by examiner

| # | Sample Rendering (Not to Scale) | Sample Exterior Dimensions | Sample Cavity Dimensions | Sample Materials | # Samples Tested | Syngina Fluid Ave. Absorption Capacity(g) | Syngina Fluid Ave. Absorption (g/g) | Synthetic Fluid Ave. Absorption Capacity (g) | Synthetic Fluid Ave. Absorption (g/g) |
|---|---|---|---|---|---|---|---|---|---|
| | Sample Menstrual Device Embodiment Descriptions and Absorbent Capacity (g) and Gram per Gram (g/g) | | | | | | | | |
| 1 | | 1.5" length; 1.75" proximal end diameter | .25" in length, 1" proximal end diameter | Frame: FXI Aquazone 4lb | 10 | 18.8 | 6.1 | 31.9 | 10.2 |
| 2 | | 2" length; 1.75" proximal end diameter | .5" in length, 1" proximal end diameter | Frame: FXI Aquazone 4lb | 10 | 23.6 | 6.5 | 37.5 | 10.4 |
| 3 | | 2" length; 1.75" proximal end diameter; | .25" in length, 1" proximal end diameter | Frame: FXI Aquazone 4lb | 10 | 22.4 | 5.9 | 31.7 | 8.3 |
| 4 | | 1.5" length; 1.75" proximal end diameter; flanges are 0.5" in total length | 0.25" in length, 1" proximal end diameter | Frame: FXI Aquazone 4lb | 10 | 15 | 5.8 | 25.4 | 9.8 |
| 5 | | 1.5" length; 1.75" proximal end diameter; flange are 0.5" in total length | .5" in length, 1.08" proximal end diameter | Frame: FXI Aquazone 4lb | 10 | 15 | 5.8 | 24.3 | 9.3 |

FIG. 23

| # | Sample Rendering (Not to Scale) | Applicator Used | Sample Exterior Dimensions | Sample Cavity Dimensions | Sample Materials | # Samples Tested | Ave. Ejection Force | STD. Deviation |
|---|---|---|---|---|---|---|---|---|
| | | | Sample Menstrual Device Embodiment Descriptions and Ejection Force Data | | | | | |
| 1 | 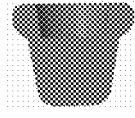 | GENTLE GLIDE ULTRA | 1.75" length; 1.75" proximal end diameter; flange are 0.5" in total length | .5" in length, 1.08" proximal end diameter | Frame: FXI Aquazone 4lb | 5 | 36.84 | 4.23 |
| 2 |  | POISE IMPRESSA | 1.75" length; 1.75" proximal end diameter; flange are 0.5" in total length | .5" in length, 1.08" proximal end diameter | Frame: FXI Aquazone 4lb | 5 | 29.23 | 4.85 |
| 3 | 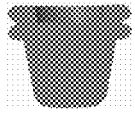 | GENTLE GLIDE ULTRA | 1.75" length; 1.75" proximal end diameter; flanges are 0.5" in total length | 0.25" in length, 1" proximal end diameter | Frame: FXI Aquazone 4lb | 5 | 41.51 | 7.78 |
| 4 | 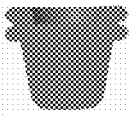 | POISE IMPRESSA | 1.75" length; 1.75" proximal end diameter; flanges are 0.5" in total length | 0.25" in length, 1" proximal end diameter | Frame: FXI Aquazone 4lb | 5 | 33.04 | 2.28 |
| 5 | 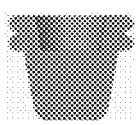 | GENTLE GLIDE ULTRA | 1.75" length; 1.75" proximal end diameter; flanges are 0.5" in total length | .5" in length, 1.08" proximal end diameter | Frame: FXI Aquazone 4lb | 5 | 32.8 | 5.24 |
| 6 |  | GENTLE GLIDE ULTRA | 1.75" length; 1.75" proximal end diameter | Upper cavity is .25" in length, 1" proximal end diameter; lower cavity is .25" in diameter, 0.95" in length | Frame: FXI Aquazone 4lb | 5 | 46.71 | 3.88 |
| 7 | 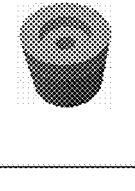 | GENTLE GLIDE ULTRA | 1.75" length; 1.75" proximal end diameter | Upper cavity is .25" in length, 1" proximal end diameter; lower cavities are each .125" in diameter, 0.95" in length | Frame: FXI Aquazone 4lb | 5 | 45.73 | 7.32 |
| 8 |  | SPORT SUPER PLUS | 1.5" proximal end diameter, 1.5" length | 1" deep, 0.75" proximal end diameter | Frame: FXI Aquazone 4lb; Seal layer: Bemis ST-804 | 10 | 17.465 | 2.143 |

*FIG. 24*

MENSTRUAL DEVICE AND APPLICATOR SYSTEM

CROSS-REFERENCE TO RELATED APPLICATIONS

This application is a continuation of U.S. patent application Ser. No. 15/602,506, filed on May 23, 2017, which claims priority to U.S. Provisional Patent Application Ser. No. 62/341,131, filed on May 25, 2016, and also to U.S. Provisional Patent Application Ser. No. 62/341,134, filed on May 25, 2016, both of which are incorporated in their entirety herein.

BACKGROUND OF THE DISCLOSURE

1. Field of the Disclosure

Aspects of the present disclosure generally relate to feminine hygiene products. More particularly, the present disclosure relates to feminine hygiene products relating to menstruation.

2. Description of Related Art

There are various types of devices that are currently used in an effort to prevent a flow of fluid (e.g. menses) from soiling a user's clothing. Two of the more common devices used for such a purpose are a tampon and a menstrual cup. A tampon operates on a principle of absorbing bodily fluids, whereas a menstrual cup operates on a principle of collecting bodily fluids.

Tampons have gained wide acceptance in the overall feminine care market based at least in part on the relative ease of disposal following use, the tendency of a tampon to conform to the user's individual anatomy, and the potential ease of insertion via an "applicator" (sometimes referred to as an "inserter" in the art). However, in some instances tampons may have a tendency to dry a user's vaginal wall, and may have a limited effective utilization time period (e.g., depending on the volume of menstrual flow). Prior art menstrual cups, on the other hand, are typically not associated with vaginal wall dryness and generally can be effectively used for longer periods of time relative to a tampon. However, relative to tampons, menstrual cups are typically more difficult to insert, can be messy to remove from the user, and typically do not accommodate an individual user's particular anatomy very well.

Suffice it to say, there are no devices currently available that provide the comfort, familiarity, and ease of insertion and removal of a tampon combined with the extended duration of use and/or fluid retention capacity of a menstrual cup.

SUMMARY OF THE DISCLOSURE

According to an aspect of the present invention, a menstrual device is provided that includes a frame and a fluid barrier seal. The frame has a side wall with an exterior surface. The side wall extends between a proximal end and a distal end. In some embodiments, the frame has an interior surface that at least in part defines an interior cavity. The fluid barrier seal (i.e., a layer or a coating) is disposed on the exterior surface of the side wall. In such embodiments, the interior cavity enables the collection and storage of more viscous fluids such as menses. The fluid barrier seal layer is disposed on the exterior surface of the side wall. The menstrual device is configurable in a compact configuration and in an expanded configuration. The expanded configuration can be an at-rest configuration or a deployed configuration. In an expanded configuration, the menstrual device is able to collect and store fluid and as such, has a storage volume greater than zero. In an expanded configuration, in embodiments having an interior cavity, the interior cavity has a volume greater than zero.

In some embodiments, the frame is an absorbent material, having a predetermined shape. In some embodiments, the frame is a flexible yet resilient material that assists in providing structure.

According to another aspect of the present invention, a menstrual device includes a frame having a support element that forms at least portions of the side wall. The side wall extends between a proximal end and a distal end. In some embodiments, the frame includes a support element and an absorbent material for the collection and storage of fluid. In some embodiments, the frame has an interior surface at least in part defines an interior cavity. In such embodiments, the interior cavity enables the collection and storage of more viscous fluids such as menses. In further embodiments having a support element, the menstrual device further includes the fluid barrier seal layer is disposed on the side wall thereby defining at least portions of the exterior surface of the menstrual device. In some embodiments, a single material can act as the fluid barrier seal layer and/or the support element.

According to another aspect of the present invention, a menstrual device system is provided that includes the aforementioned menstrual device and an applicator. The applicator has an insertion tip end, a barrel region and a finger grip region defined by a plunger end. The applicator has a plunger that telescopically engages the interior of the applicator barrel and interacts with the menstrual device. The applicator is configured to receive the menstrual device and retain the menstrual device in a compact configuration. Prior to being loaded into the applicator, the menstrual device is in an at-rest configuration. Upon insertion into the body, the applicator (via the plunger exerting a force at the distal end of the menstrual device) ejects the menstrual device into the body such that the menstrual device expands (i.e. is in an expanded configuration).

BRIEF DESCRIPTION OF THE DRAWINGS

FIG. 23 is a chart describing the sample menstrual device embodiment descriptions and absorbent capacity.

FIG. 24 is a chart describing the sample menstrual device embodiment descriptions and ejection force data.

DETAILED DESCRIPTION OF THE DISCLOSURE

Figure 1:
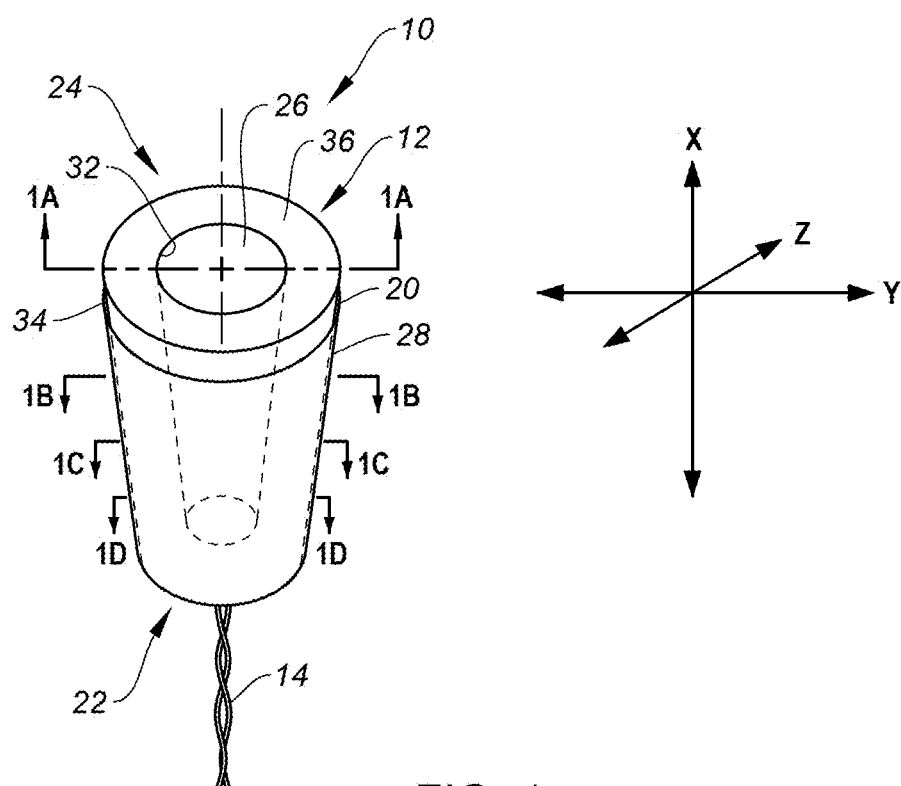
FIG. 1 is a diagrammatic angled view of a menstrual device embodiment according to the present disclosure.

Referring to the drawings, according to an aspect of the present disclosure a menstrual device 10 is provided that includes a frame 12 and at least one removal element 14. The menstrual device 10 and frame 12 provide for the collection of fluids. "Collecting" or "collection" and other tenses as used throughout the present disclosure, is defined as the ability to collect fluids within the menstrual device 10 by either retaining fluids and/or absorbing fluids. The term "absorbing" or "absorbent" and other tenses as used throughout the present disclosure, is defined as a porous material having the ability to hold fluids inside a material's matrix, such that fluid ingratiates the material's structure and/or resides within pores or interstitial voids between the material's structure. The term "retain" or "retention" and other tenses as used throughout the present disclosure, is defined as the ability to hold fluid within the device like, for instance, a cup.

In some embodiments, the menstrual device 10 and frame 12 provide for the retention of fluids. In some embodiments, the menstrual device 10 may also include an absorbent material 16 (see FIGS. 4 and 4A) and/or an absorbent article 18 (see FIGS. 5 and 5A).

Referring to FIGS. 1, 3A-5B, embodiments of the present menstrual device 10 include a frame 12 having at least one side wall 20, a distal end 22, a proximal end 24, an interior cavity 26, and a seal layer 28. The side wall 20 has a thickness 30 extending between an interior surface 32 and an exterior surface 34. The proximal end 24 has a proximal end surface 36. In some embodiments (e.g., see FIGS. 1, 1A, 2, 2A, 4, and 4A), the distal end 22 includes an interior surface 38 and an exterior surface 40, and a thickness 42 that extends there between. The distal end 22 of the frame 12 is closed; e.g., the interior cavity 26 is not accessible through the distal end 22 (i.e., is fluid impermeable at the distal end 22). The proximal end 24 of the frame 12 may be described as being "open" in an expanded configuration (as will be described below) in that the interior cavity 26 is accessible through the proximal end 24 of the frame 12; e.g., open to allow the collection of menstrual fluids within the interior cavity 26.

Figure 1A:
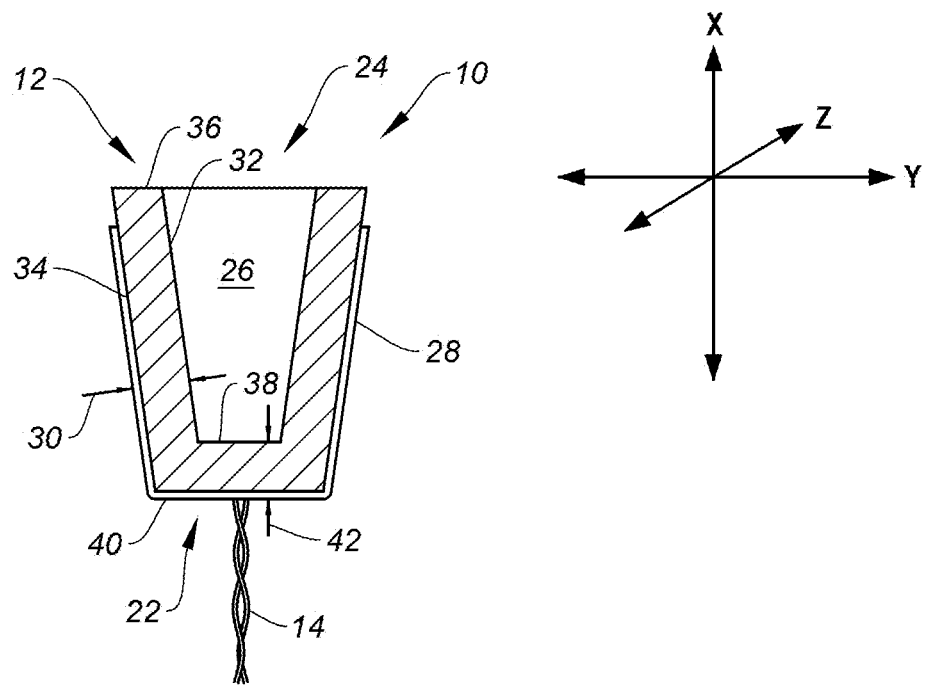
FIG. 1A is a diagrammatic lengthwise sectional view of the menstrual device embodiment shown in FIG. 1.
Figure 1B:
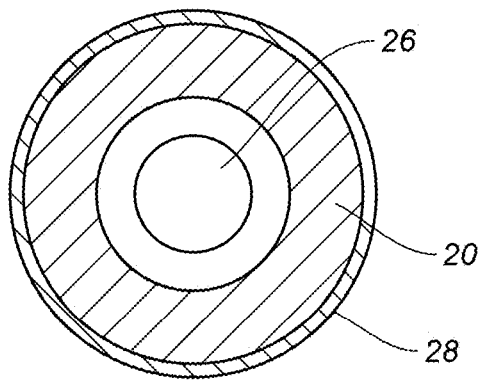
FIG. 1B-1D are diagrammatic axial sectional views of the menstrual device embodiment shown in FIG. 1.
Figure 1C:
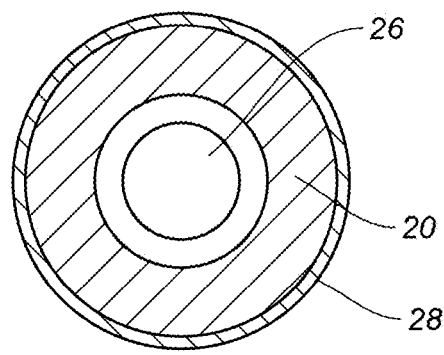
Figure 1D:
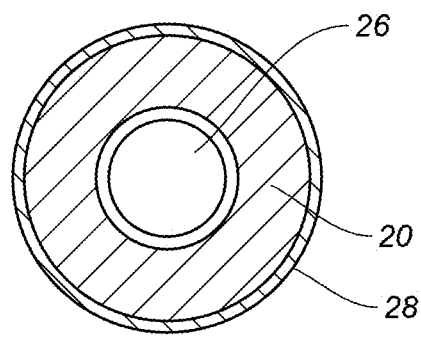
Figure 3A:
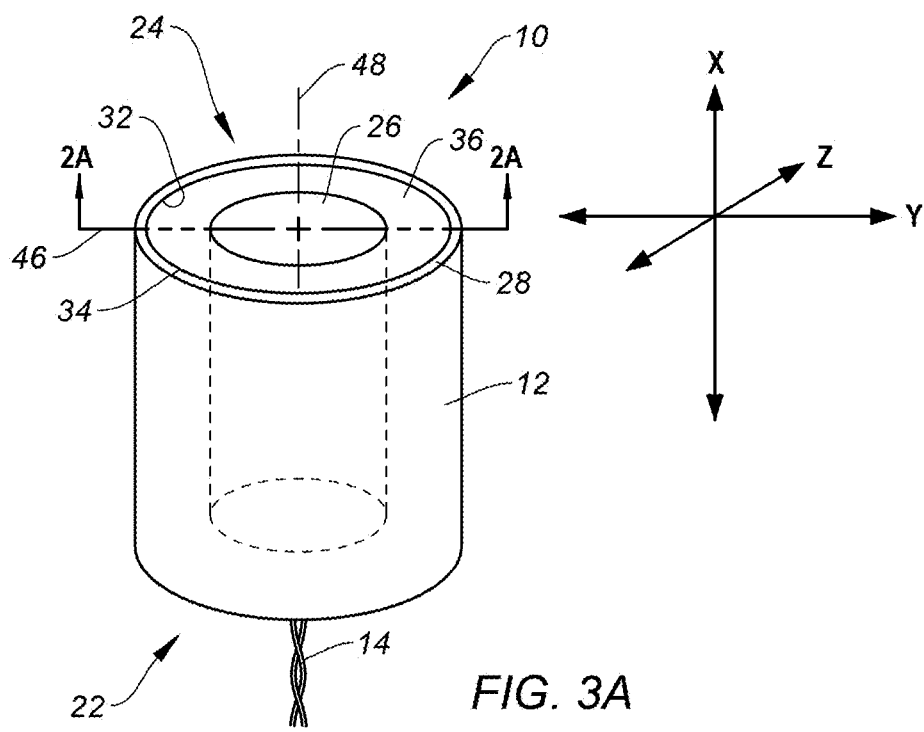
FIG. 3A is a diagrammatic angled view of a menstrual device embodiment according to the present disclosure.
Figure 3B:
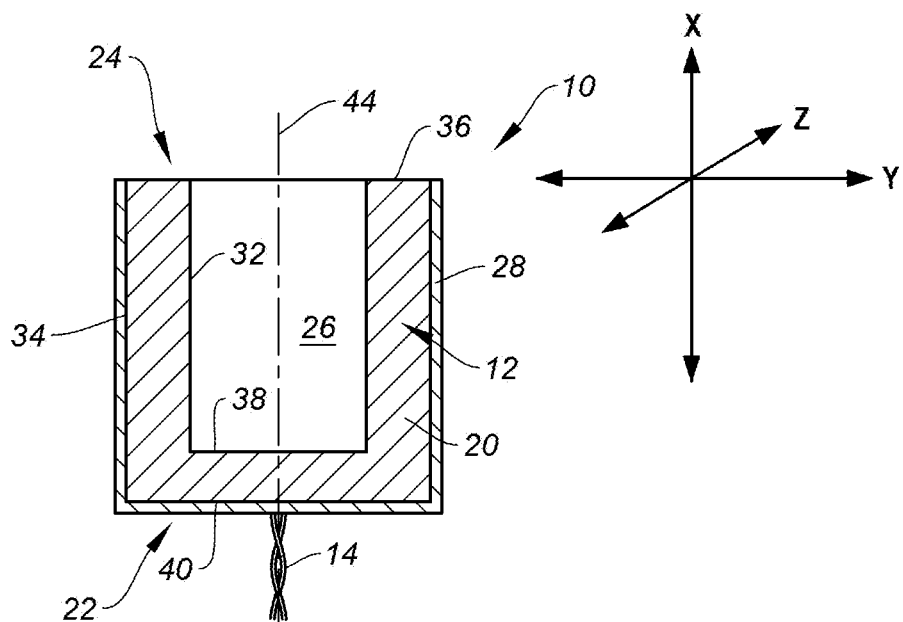
FIG. 3B is a diagrammatic lengthwise sectional view of the menstrual device embodiment shown in FIG. 2.

To facilitate the description herein, the menstrual device 10 will be described herein as having a lengthwise axis 44 that extends along an X-axis, a widthwise axis 46 that extends along a Y-axis, and a depthwise 48 axis that extends along a Z-axis (see FIGS. 1 and 1A). As will be described below, the menstrual device 10 may assume a variety of different geometric shapes. In each of these shapes, the menstrual device 10 (and therefore the frame 12) may assume a plurality of configurations; e.g., a "compact configuration", a "deployed configuration", and an "at rest configuration". The particular geometric shape of a menstrual device is visible when the menstrual device is its' "at rest configuration". To facilitate description of these different menstrual device geometric shapes, as well as the respective configurations of each, the menstrual device 10 (and therefore the frame 12) may be described as having a cross-sectional area (i.e., in the Y-Z plane). Depending on the particular geometric shape of the menstrual device 10, in the deployed and at rest configurations, the cross-sectional area of the menstrual device 10 may differ at different lengthwise positioned sections (e.g., see sectional views 1B-1B, 1C-1C, 1D-1D, etc.; e.g., a truncated conical shaped device as shown in FIGS. 1 and 1A), or the cross-sectional area may be equal at different lengthwise positioned sections (e.g., a tubular shaped device as shown in FIGS. 3A and 3B).

Figure 2:
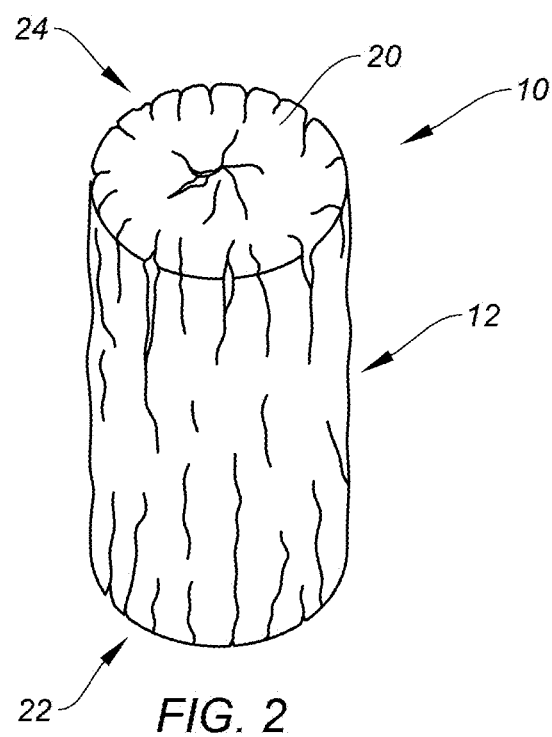
FIG. 2 is a diagrammatic view of a menstrual device according to the present disclosure shown in a compact configuration.

A menstrual device 10 configured in a "compact configuration" is shown in FIG. 2. The term "compact configuration" as used herein refers to a configuration wherein the frame 12 of the menstrual device 10 is elastically deformed (e.g., by squeezing, compressing, or folding the frame 12) to an extent wherein the interior cavity 26 has a volume less than is present in a deployed configuration. "Elastic" as used herein, describes strain a material can recover from, contrasted to strain that causes the material to plastically deform. In some instances when the menstrual device 10 is in a compact configuration, the interior cavity 26 has a "zero" value cavity volume; e.g., the side wall interior surfaces 32 come together with no volume there between, or said differently, the cavity is obfuscated. As will be evident from the description below, in some embodiments the frame 12 may be elastically deformed (e.g., compressed) to not only have a zero interior cavity 26 volume, but also the frame 12 may be elastically deformed further to assume a lesser volume; e.g., a configuration having a zero interior cavity 26 volume and compressed side walls. In some instances when the menstrual device 10 is in a compact configuration, the interior cavity 26 has a volume (e.g., the side wall interior surfaces 32 do not completely come together), but that volume is less than the interior cavity 26 would have in a deployed configuration. To facilitate the description of the present menstrual device 10, a menstrual device 10 in a compact configuration may be described as occupying a first volume.

Figure 1E:
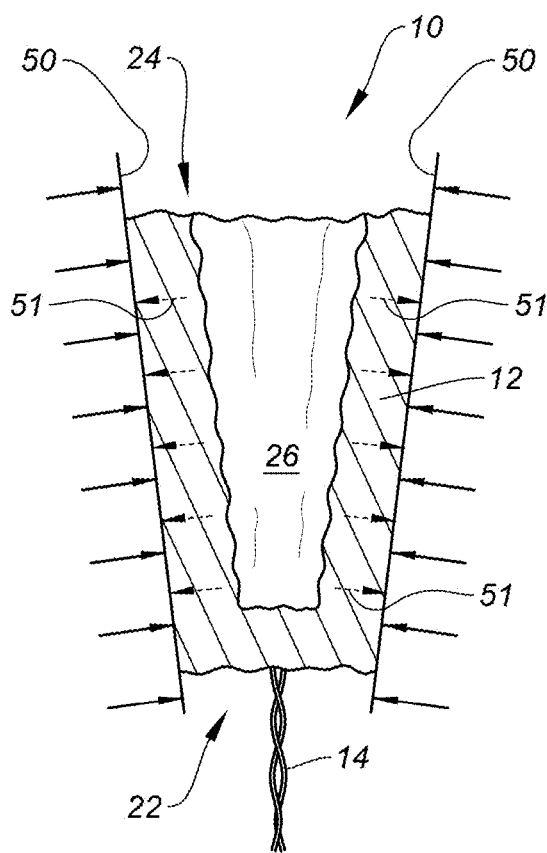
FIG. 1E is a diagrammatic lengthwise sectional view of the menstrual device embodiment shown in FIG. 1, shown in a slightly compressed configuration.

A menstrual device 10 in a "deployed configuration" can be seen in FIG. 1E. In the deployed configuration, the menstrual device 10 is in a partially compressed configuration; i.e., assuming a volume less than the volume of the same device at rest, but more volume than the same device in a compact configuration. FIG. 1E diagrammatically shows forces acting on the exterior surface 34 of the device 10 that cause the device to be in a slightly compressed configuration; i.e., a deployed configuration. The term "deployed configuration" refers to a menstrual device 10 configuration that may be assumed under normal use conditions; e.g., a configuration that may be typically assumed during use of the device when the device 10 is located in its intended functional position. In a deployed configuration, menstrual device 10 embodiments that include an interior cavity 26: a) have an interior cavity 26 volume greater than zero (e.g., at least some side wall interior surface 32 portions are separated from one another to create a greater than zero volume there between); and b) have an interior cavity 26 that is open (i.e., accessible) at the proximal end 24 of the frame 12. The menstrual device 10 in a deployed configuration has less than or equal to one hundred percent (100%) of the "at rest" configuration's dimensions and/or volume. The menstrual device 10 in a deployed configuration can be described as occupying a second volume that is greater than a first volume.

A menstrual device 10 in an "at rest" configuration is shown in FIGS. 1, 3A, 4A, and 5A. The term "at rest" as used herein refers to the configuration a menstrual device 10 assumes by itself (i.e., expands to) when no external forces are applied to the menstrual device 10, therefore the device 10 is at rest and geometrically stable (e.g., no applied forces acting on the device 10 that prevent the frame 12 from further expanding). In an at rest configuration, device 10 embodiments having an interior cavity 26 will have an interior cavity volume greater than zero. In an at rest configuration, the interior cavity 26 is open (i.e., accessible) at the proximal end 24 of the frame 12. In an at rest configuration the menstrual device can be described as having a third volume that is greater than the first volume, and/or greater than or equal to the second volume.

The frame 12 is configured such that in the absence of applied forces holding the frame 12 in a compact configuration, the frame 12 will by itself elastically change from a compact configuration to a deployed configuration (i.e., where some amount of applied forces are still applied to the device 10 that prevent the device 10 from completely expanding to an at rest configuration), or will completely elastically expand to an at rest configuration (e.g., the configuration independently assumed in the absence of forces applied to the device 10).

The ability of the frame 12 to elastically expand (e.g., from a compact configuration to a deployed configuration or an at rest configuration) does not utilize any liquid (absorbed or otherwise incorporated into the frame 12) as a mechanism of change. In some embodiments, the elastic expansion of the frame 12 is accomplished by the frame 12 unfolding. In some embodiments, the elastic expansion of the frame 12 is a function of the frame material being inherently elastically expandable between a compressed configuration (e.g., a compact configuration) and an expanded configuration (e.g., a deployed configuration or an at rest configuration). In some embodiments, the ability of the frame 12 to elastically expand may be a combination of these mechanisms, or other mechanisms.

Figure 4A:
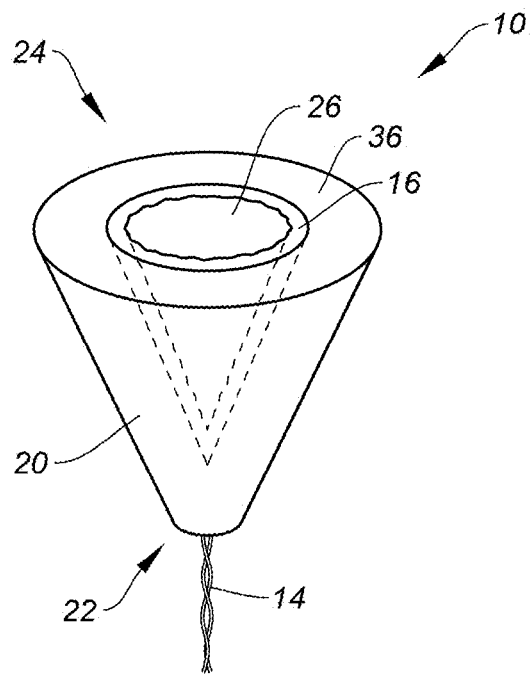
FIG. 4A is a diagrammatic angled view of a menstrual device embodiment according to the present disclosure.
Figure 4B:
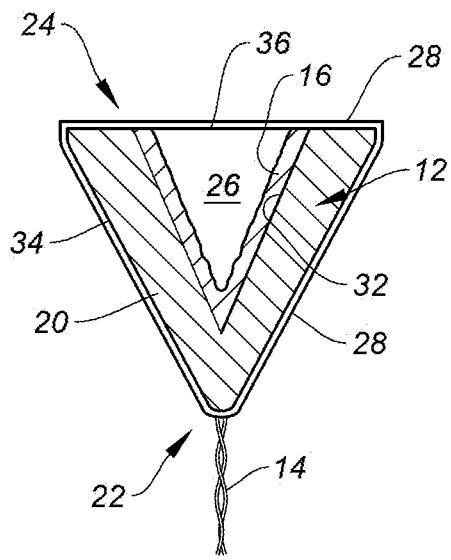
FIG. 4B is a diagrammatic lengthwise sectional view of the menstrual device embodiment shown in FIG. 3.

In some embodiments, the interior cavity 26 and therefore the volume of the interior cavity 26 is completely defined by the interior surface 32 of the side wall 20 (e.g., see FIGS. 4A and 4B). In those embodiments where the distal end 22 of the frame 12 includes an interior surface 38 and an exterior surface 40 (e.g., see FIGS. 1, 1A, 3A, 3B, 5A, and 5B), the interior cavity 26 (and its volume) is defined by the interior surface 32 of the side wall 20 and the interior surface 38 of the distal end 22.

The frame 12 comprises one or more materials, which collectively have mechanical material properties that enable the frame 12 to: a) be elastically deformed or folded into a compact configuration; and b) in the absence of applied forces holding the frame 12 in a compact configuration, self-expand into an expanded configuration; e.g., without utilizing any liquid (absorbed or otherwise incorporated into the frame 12) as a mechanism of change. An example of an acceptable frame material is an elastic polymer that can be formed into a geometric shape useful for a menstrual device 10; e.g., an elastic polymer formed to assume a desired geometric shape and volume in an at rest configuration (i.e., in the absence of applied forces) and which polymer can be elastically compressed to a smaller volume and thereby assume a reduced volume configuration (e.g., a deployed configuration or a compact configuration). Specific non-limiting examples of elastic polymers include medical grade and/or biocompatible polyester, polyvinyl alcohol (PVA), polypropylene, polyacrylate, or polyurethane foams such as aliphatic that resist changes in color and/or aromatic, and/or starch-based foams such as those made from crosslinked polysaccharides. The term "foam" as used herein refers to a substrate construction having internal voids, which voids may vary in size and number per volumetric unit.

The mechanical material properties of the frame material(s) that enable the frame 12 to elastically expand from a compact configuration to an expanded configuration may be described in terms of "expansion forces". To illustrate, consider a frame 12 maintained in a deployed configuration (e.g., see FIG. 1E, wherein the menstrual device 10 assumes a volume less than the volume of the same device in an at rest configuration). Body wall surfaces 50 (e.g., vaginal wall surfaces) in contact with the menstrual device 10 to potentially prevent the menstrual device 10 from assuming its fully expanded configuration (i.e. the at-rest configuration), and thereby maintain the menstrual device 10 in the partially compressed deployed configuration. The vaginal cavity is known to typically exert a pressure between about 0.25 psi and about 1.0 psi. As a result, the expansion forces 51 that would otherwise cause the menstrual device 10 to elastically expand to an at rest configuration, now act against the body wall surfaces 50. Those expansion forces 51, which are quantifiable, are at least a part of the mechanism that enables the menstrual device 10 to be maintained at a particular position within the user's vagina. It should be noted from the above that menstrual devices 10 according to the present disclosure are intended to assume an expanded configuration, albeit one that is potentially partially compressed configuration (i.e. a deployed configuration), during in vivo use. The expansion forces 51 are described as being "at least part of the mechanism" that enables the device to be positionally retained because other factors may also play a part in retaining the device; e.g., the coefficient of friction of the exposed surface of the seal layer 28, the coefficient of friction of the body wall surface 50, the geometric shape of the menstrual device 10, etc. For the present menstrual device embodiments, the frame 12 is chosen to have mechanical material properties (as described above) that produce expansion forces adequate to retain the device 10 in vivo in a deployed configuration, while at the same time such expansion forces 51 are below a magnitude that: a) would cause user discomfort; b) inhibit or prevent the menstrual device 10 from being placed in a compact configuration (e.g., for insertion purposes with or without an applicator); and/or c) inhibit removal of the menstrual device 10 from an in vivo deployment. The expansion forces 51 produced by the frame material are further discussed below in the context of an applicator device that may be used with the present menstrual device 10.

Figure 5A:
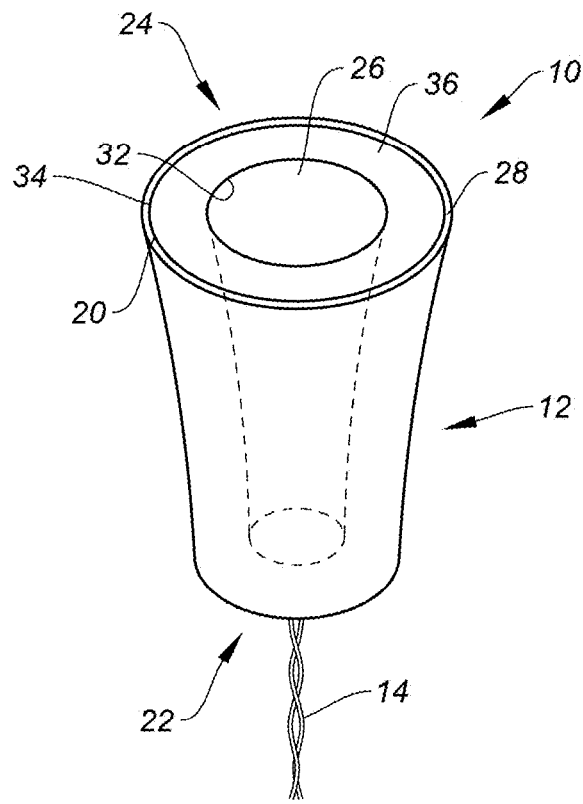
FIG. 5A is a diagrammatic angled view of a menstrual device embodiment according to the present disclosure.
Figure 5B:
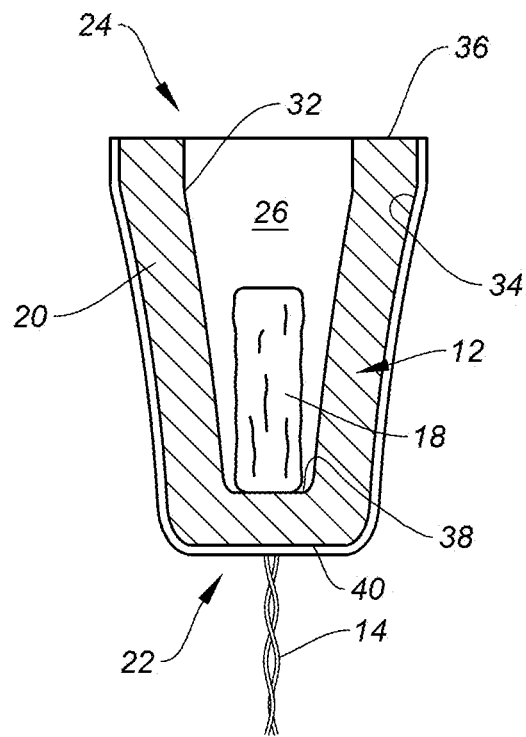
FIG. 5B is a diagrammatic lengthwise sectional view of the menstrual device embodiment shown in FIG. 4.

As indicated above, the frame 12 (and therefore the menstrual device 10) may assume a variety of different geometric shapes three-dimensionally and/or in profile or cross-section (i.e. cup-like, conical, tubular, funnel-shaped, tapered and/or shaped), all of which shapes include the interior cavity 26. FIGS. 1 and 1A, for example, show a frame 12 in an enlarged configuration having a truncated conical shape. FIGS. 3A and 3B show a frame 12 in an enlarged configuration having a tubular shape. FIGS. 4A and 4B show a frame 12 in an enlarged configuration having a conical shape. In some embodiments as those exemplified in at least FIGS. 3A and 3B, the menstrual device has symmetry about its vertical axis (i.e. X axis). FIGS. 5A and 5B show a frame 12 in an enlarged configuration having a widthwise dimension that is non-linearly variable along the length of the device. The present menstrual device 10 is not limited to these particular geometric shapes. In FIGS. 1, 1A, 3A, 3B, 4A, 4B, 5A, and 5B, the frame 12 is shown as being symmetrical within the Y-Z plane; i.e., the Y and Z dimensions are identical or nearly identical. In alternative embodiments, the present menstrual device 10 may have a geometric shape that is non-symmetrical in the Y-Z plane; e.g., the width dimension (i.e., the Y direction) may be greater than the depth dimension (i.e., the Z direction); e.g., an oval shape. In addition, or alternatively, the geometric shape may be non-symmetrical along its length; e.g., cross-sectional Y-Z plane geometries may vary at different lengthwise positions. For example, the geometric shape of the frame 12 may be customized for in-vivo placement for enhanced sealing performance; e.g., shaped to have a geometric shape that conforms with a particular shape associated with a vaginal region where the device is intended to be deployed.

As indicated above, menstrual devices 10 according to the present disclosure are intended to assume an expanded configuration (e.g., a deployed configuration), albeit one that is potentially partially compressed, during in vivo use; it is possible the menstrual device 10 could be fully expanded about a portion or a region, and/or fully expanded, as anatomy of the vaginal canal varies. Nonetheless, based on in vivo testing identifying anatomical features, dimensions, it is likely the menstrual device 10 will be partially compressed during in vivo use. The expansion forces associated with the partially compressed menstrual device 10 create a seal between the side wall exterior surfaces of the device and the user body wall surfaces 50. The aforesaid seal helps to prevent fluid passage between the side wall exterior surface and the user body wall surface 50 during use. In all menstrual device 10 embodiments having an interior cavity 26, the geometric shape of the frame 12 is such that when the device is deployed in vivo in its operational position, the interior cavity 26 of the frame 12 is open at the proximal end 24 to enable the interior cavity 26 to receive and collect menstrual fluids. It is recognized that during use, movement of the user may cause the present menstrual device 10 to deflect and potentially assume a variety of different geometric shapes. As such, in some user physical positions it is possible that the present menstrual device 10 may be compressed; e.g., into a configuration wherein the interior cavity 26 is not open at the proximal end 24. Nevertheless, the statement above regarding the interior cavity 26 of the frame 12 being open (when deployed in vivo in its operational position) reflects that the interior cavity 26 of the frame 12 is open at the proximal end 24 during most but not necessarily all possible user positions.

The frame 12 may be manufactured using a variety of different techniques. An acceptable example of such a technique is polymer molding technique wherein the frame 12 is molded to have the desired geometric configuration. Molding is particularly useful when the frame 12 is formed from an elastic polymer foam.

The menstrual device 10, in an at rest configuration, has a length along its lengthwise axis of between about 1.0 inches (25.4 mm) and about 2 inches (51 mm), and more preferably between about 1.5 inches (38 mm) and 1.75 inches (44.5 mm). In some embodiments, the length of the menstrual device is about 1.5 inches 1.6 inches or about 1.75 inches. For clarity, the length of the menstrual device 10 is from its proximal end 24 to its distal end 22 defining the fluid collection portion of the device; it does not include any additional length of the removal element 14.

The menstrual device 10, in an at rest configuration, has a proximal end 24 width dimension along the widthwise axis of between about 1.0 inches (25.4 mm) and about 2 inches (51 mm), and more preferable between about 1.5 inches (38 mm) and 1.75 inches (44.5 mm). In some embodiments, the width of the menstrual device at the proximal end is about 1.5 inches 1.6 inches or about 1.75 inches.

The menstrual device 10, in an at rest configuration, has a proximal end 24 depth dimension along the depthwise axis of between about 1.0 inches (25.4 mm) and about 2 inches (51 mm), and more preferable between about 1.5 inches (38 mm) and 1.75 inches (44.5 mm). In some embodiments, the depth of the menstrual device at the proximal end is about 1.5 inches 1.6 inches or about 1.75 inches.

In some embodiments of the menstrual device 10 in an at rest configuration, the ratio between the length and the width at the proximal end 24 is greater than 1. In other embodiments, the ratio is between about 1 and about 2. In other embodiments, the radio between the length and the width at the proximal end 24 is greater than 1. In other embodiments, the ratio is between about 1 and about 2.

The menstrual device 10, in an at rest configuration, has a distal end 22 that has less than or equal to the widthwise and/or depthwise dimension of the proximal end 24. For instance, the widthwise dimension and/or depthwise dimension at the distal end 22 is between about 0.1 inches (0.25 mm) to about 1.5 inches (38 mm). In some embodiments, the ratio of the widthwise dimension and/or depthwise dimension at the proximal end 24 to the widthwise dimension and/or depthwise dimension at the distal end 22 is between about 20:1 and 1:1. In some embodiments, this ratio is between about 10:1 and about 1:1. In other embodiments, this ratio is between about 5:1 and about 1.25:1. In further embodiments, this ratio is greater than 1. In yet further embodiments, this ratio is less than 2:1. In yet other embodiments, this ratio is about 1.25:1, about 1.5:1, or about 1.75:1.

In some embodiments, the menstrual device 10, in an at rest configuration, has a widthwise dimension and depthwise dimension, at any given cross-sectional slice in the Y-Z plane, have a ratio between the widthwise dimension and the depthwise dimension of about 1:1. Nonetheless, in a deployed configuration, this ratio may change and be between 1:2 and 2:1 depending on the anatomical geometry of a given user. This widthwise/depthwise ratio can be dynamic as the menstrual device 10 collects fluid and/or as the user moves through a variety of positions, and/or other changes the body undergoes over time throughout a given period of time when the menstrual device 10 is worn (i.e., which can be for several hours).

The cavity 26, in the at-rest configuration, has a length dimension along the lengthwise axis of between about 0.1 inches (2.5 mm) and about 1.9 inches (48 mm), or between about 0.2 inches (5 mm) and about 1.75 inches (44.5 mm), or between about 0.25 inches (6.5 mm) and about 1.25 inches (32 mm). In some embodiments, the cavity 26 has a length dimension that is less than half of the length of the menstrual device 10, or said differently, the ratio of the length of the cavity 26 to the length of the menstrual device is less than or equal to 1:2. In some embodiments, this is preferred in order to maintain resiliency in the device sufficient to go from a compact configuration to a deployed configuration such that the deployed configuration is able to exert a pressure against the vaginal wall to create a sufficient seal thereby mitigating leakage, albeit a pressure that is not otherwise uncomfortable or noticeable to the user.

Figure 22:
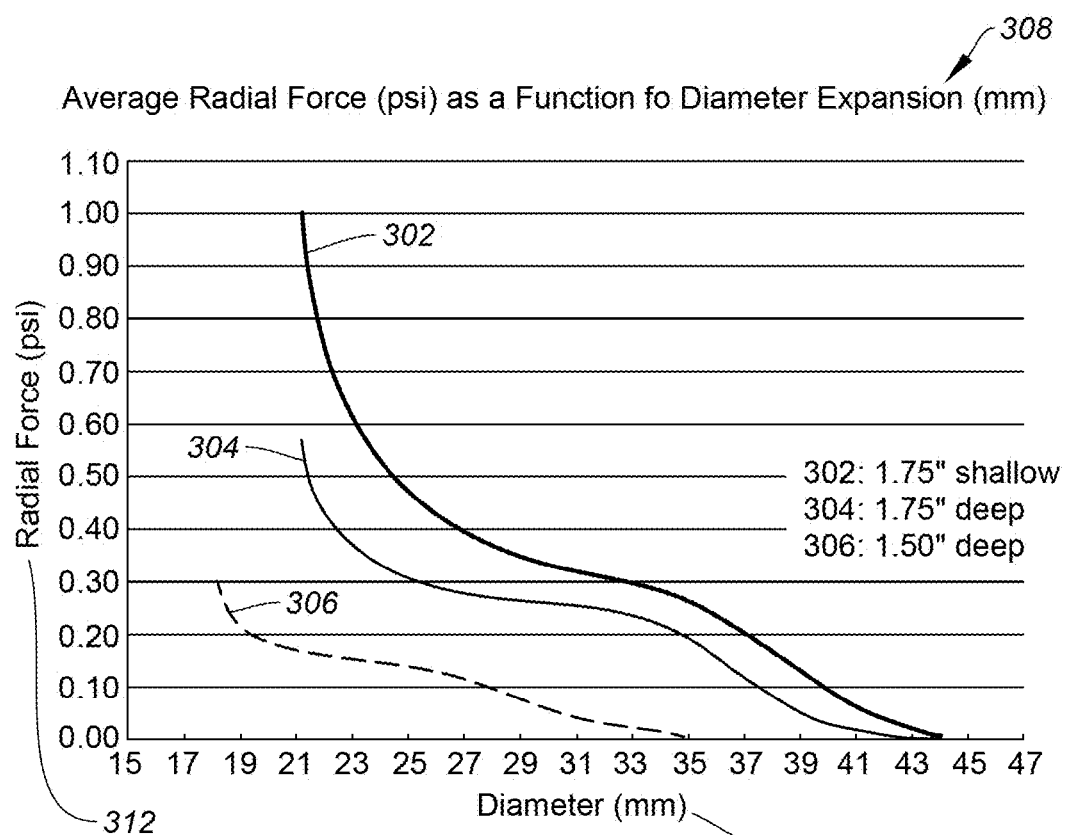
FIG. 22 is a chart describing the expansion diameter and radial force exerted by a menstrual device of the present disclosure.

FIG. 22 demonstrates how the dimensions of the menstrual device 10 provide varying expansion profiles. Specifically, FIG. 22 describes radial pressure (psi) exerted by menstrual device 10 as a function of the level of radial compaction of the menstrual device as described in the title (reference numeral 308). The horizontal axis 310 describes the diameter of the menstrual device in mm, while the vertical axis 312 describes the radial force in psi. Three samples having a frame material including AQUAZONE 41b foam made by FXI were tested, where the highest curve labeled "302" regards a menstrual device that is 1.75 inches in length, with a cavity having a length of 0.25 inches, the middle curve labeled "304" regards a menstrual device that is 1.75 inches in length, with a cavity having a length of 0.50 inches, and the lowest curve labeled "306" regards a menstrual device that is 1.50 inches in length, with a cavity having a core that is 0.50 inches in length. If one reads FIG. 22 from right to left, one notes the diameter in the at-rest configuration of the three samples. Moving towards the vertical axis (i.e., from right to left), one sees each of the three samples undergoing radial compression, and as the compressive force is applied (thereby reducing the diameter of each sample) a force is exerted. The 1.75 inch sample with the shallowest cavity provided the greatest amount of resistance to compression (or the ability to apply the greatest radial pressure of the samples), while the 1.5 inch sample with a deeper cavity provided the least amount of resistance (or the ability to apply the lowest radial pressure of the samples). Nonetheless, the data demonstrates the menstrual device 10 of the present disclosure provides a radial pressure that assists in creating a seal with the vaginal wall of at least 0.3 psi, enough to provide an opposite force of similar magnitude to that of the vaginal wall. In some embodiments, a pressure of at least 0.50 psi is provided, and in further embodiments, a pressure of at least 1.00 psi is provided. In some embodiments, the menstrual device 10 of the present disclosure is able to provide a pressure of at least 0.25 psi with a deployed configuration diameter of at least 31 mm (or 70% of its at-rest diameter).

In some embodiments, it is preferred to have a cavity 26 having a length dimension that is greater than 0.25 inches due to the relatively slow fluid penetration times of the frame 12 material, as measured by a high speed camera, distilled water, and a goniometer such as Model DSA100 made by Kruss, having a needle providing a 55 ml drop size where the needle tip is positioned a distance of 9 mm from the proximal end 24 of the menstrual device 10. For instance, a 1" by 1" cubic sample of AQUAZONE foam material (density of 4 pounds) made by FXI has a fluid penetration time that is about four times slower than a regular absorbency tampon branded TAMPAX PEARL made by Procter & Gamble, demonstrating some embodiments of the menstrual device 10 of the present disclosure have a frame 12 with distinct fluid handling characteristics than that of typical tampon pledgets made of rayon, cotton, or the like. As such, the cavity 26 provides a reservoir to retain fluid and increase the exposed surface area of the frame 12 while permitting the frame 12 to absorb fluid. In some embodiments, the ratio of the exposed surface area provided by the cavity 26 versus the surface area of just the proximal end 24 (in embodiments without a cavity) is between about 2.5:1 to about 1:1, or is greater than 1:1, or is less than 2:1, or is about 1.2:1.

In some embodiments such as those shown in FIGS. 3A and 3B, the cavity 26 is a single lengthwise cavity that is generally tubular such that the widthwise and/or depthwise dimension at the proximal end 24 is about equal to the widthwise and/or depthwise dimension at the distal end 22. In other embodiments such as those demonstrated in FIGS. 4A-5B, the cavity 26 has a taper such that the cavity 26 has a greater widthwise and/or depthwise dimension at the proximal end 24 than at the distal end 22. The cavity 26 has a ratio of the widthwise and/or depthwise dimension at the proximal end 24 to the widthwise and/or depthwise dimension at the distal end 22 is between about 20:1 and 1:1. In some embodiments, this ratio is between about 10:1 and about 1:1. In other embodiments, this ratio is between about 5:1 and about 1.25:1. In further embodiments, this ratio is greater than 1. In yet further embodiments, this ratio is less than 2:1. In yet other embodiments, this ratio is about 1.25:1, about 1.5:1, or about 1.75:1.

Figure 6:
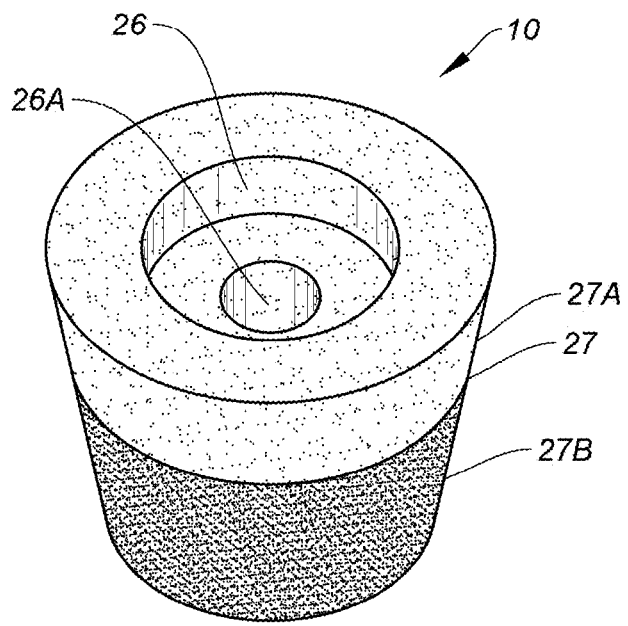
FIG. 6 is a diagrammatic angled view of a menstrual device embodiment according to the present disclosure.
Figure 7:
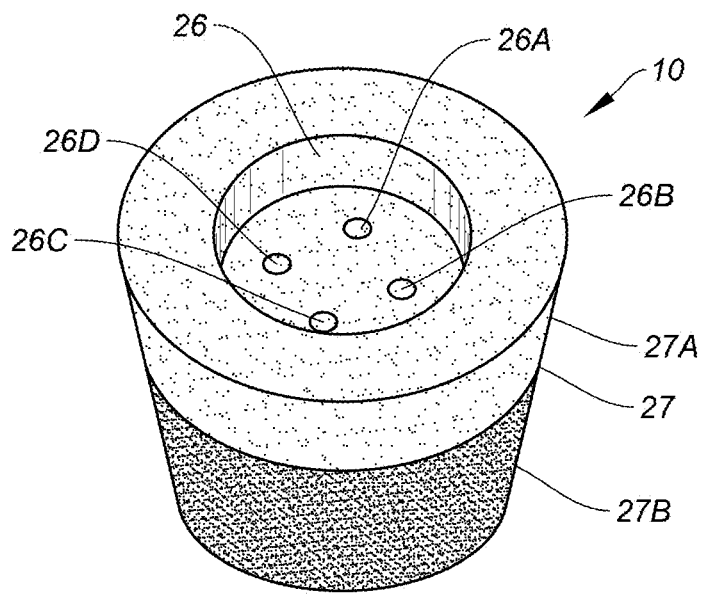
FIG. 7 is a diagrammatic angled view of a menstrual device embodiment according to the present disclosure.
Figure 8A:
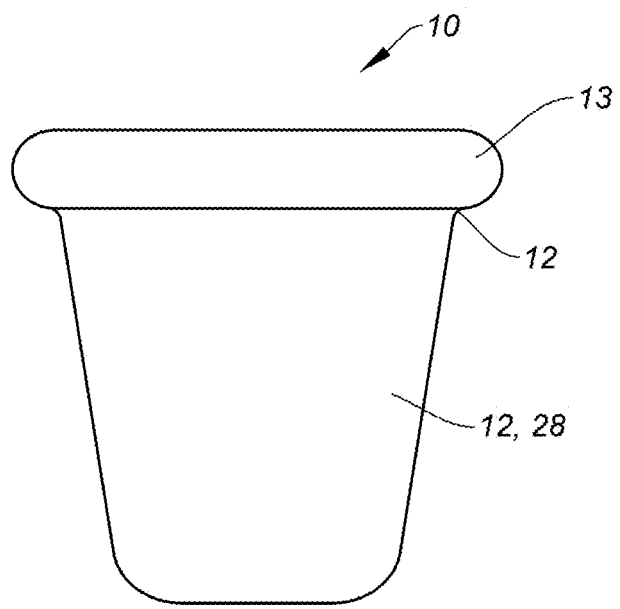
FIG. 8A is a diagrammatic side view of a menstrual device embodiment according to the present disclosure.
Figure 8B:
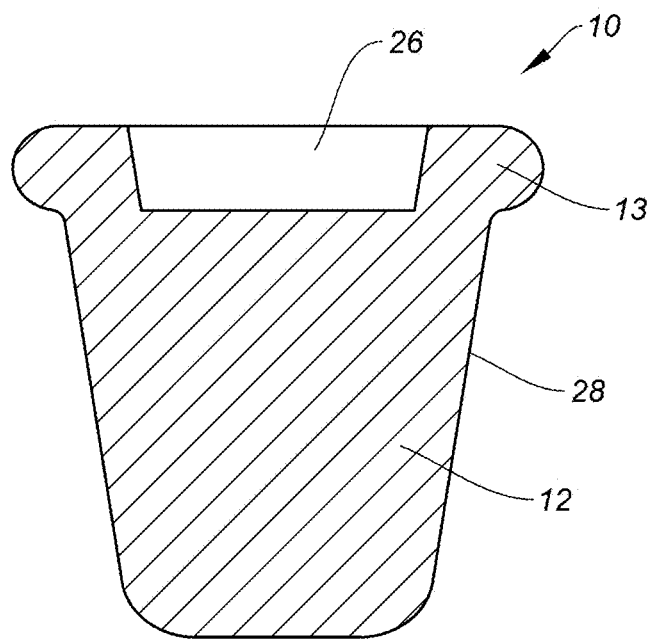
FIG. 8B is a diagrammatic lengthwise sectional view of the menstrual device embodiment shown in FIG. 8A.
Figure 9A:
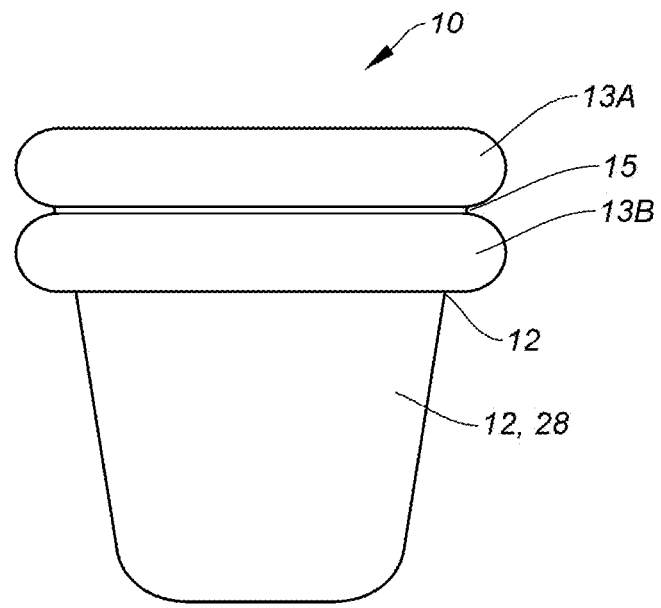
FIG. 9A is a diagrammatic side view of a menstrual device embodiment according to the present disclosure.
Figure 9B:
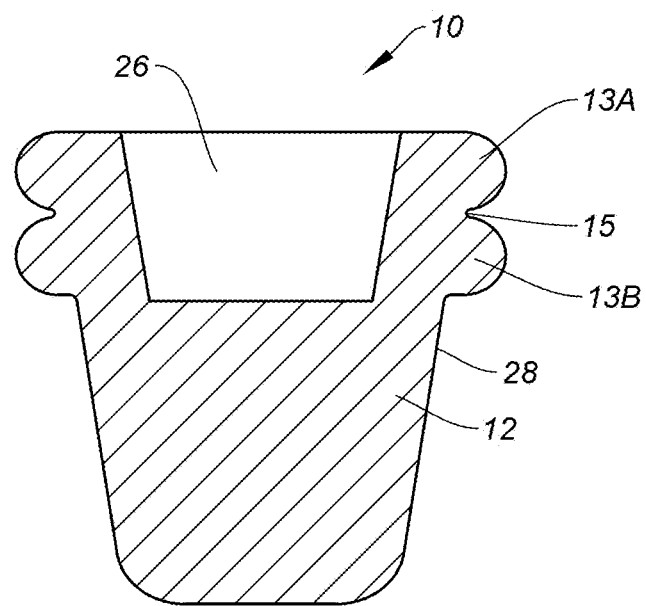
FIG. 9B is a diagrammatic lengthwise sectional view of the menstrual device embodiment shown in FIG. 9A.

In other embodiments as exemplified in FIGS. 6 and 7, the cavity 7 has a step-change 27 in widthwise and/or depthwise dimension [as one moves along the length of the menstrual device 10 from a proximal end 24 to the distal end 22]. For exemplary purposes, the step change 27 is shown by the change in color (i.e., the lighter grey indicates a location 27A above step-change 27, and the darker grey indicates a location 27B below the step-change 27). The step-change 27 in widthwise and/or depthwise dimension describes an abrupt change in such dimension (i.e. not a gradual taper). In some embodiments having a single cavity 26 above the step change 27 to a single cavity 26 below the step change 27 (i.e. as exemplified in FIG. 6 and/or with respect to one of the four cavities 26A, 26B, 26C, and/or 26D in FIG. 7), the cavity 26 has a ratio of the diameter of the widthwise and/or depthwise dimension at a location 27A immediately above the step change 27 of to the widthwise and/or depthwise dimension at a location immediately below 27B the step change 27 of between about 30:1 to about 2:1, or between about 25:1 to about 5:1, or between about 15:1 to about 8:1.

In other embodiments, a step-change 27 in widthwise and/or depthwise dimension [as one moves along the length of the menstrual device 10 from a proximal end 24 to the distal end 22] involves a change in the number of cavities. As exemplified in FIG. 7, cavity 26 becomes four cavities 26A-26D. The number of cavities 26 can vary from one to a plurality, keeping in mind typical cavities are at least 0.1 inches (in a minimum widthwise and/or depthwise dimension if the cavity is not constant along the lengthwise axis) and up to about 0.9 inches (in a maximum widthwise and/or depthwise dimension if the cavity is not constant along the lengthwise axis) in widthwise and/or depthwise dimension and need to be spaced apart to ensure the cavities do not collapse upon each other. In one embodiment, the ratio of the surface area of the cavity 26 immediately above 27A the step-change 27 to the surface area of the cavity (or all cavities) 26 immediately below 27B the step-change 27 is between about 18:1 and 2:1, or less than or equal to about 10:1, or greater than or equal to about 2:1.

In embodiments having a single cavity 26 immediately above 27A a step-change 27 and at least two cavities (i.e. 26A, 26B) immediately below 27B the step-change 27, the ratio of the surface area of the cavity 26 immediately above 27A the step-change 27 to the surface area of the cavities (i.e. 26A, 26B) below 27B the step-change 27 is between about 18:1 and 1:1, or between about 10:1 and 1.5:1, or less than about 10:1, or greater than about 1.1:1.

Another aspect of the menstrual device 10 of the present disclosure is that it is distinct from commercially available internally worn menstrual devices in where fluid collects first. As with commercially available tampon pledgets, fluid is typically absorbed into the pledget at the top region of the pledget (i.e. the proximal end) and travels downward towards the bottom of the pledget. In other words, commercially available pledgets absorb fluid in the top region first, and fluid thereafter travels downward. Commercially available menstrual cups act oppositely. Fluid is retained within the menstrual cup and pools at the bottom and fills upward. The menstrual device of the present disclosure collects fluid differently, in part due to the fact that it collects fluids. In embodiments with cavities, the fluid collects in the middle region of the pledget (i.e. not solely at the proximal surface of a tampon pledget, and not solely by filling from the bottom-up of the menstrual cup). In embodiments where the cavity 26 (or cavities 26) have a length that is at least about 10% and up to about 90% of the length of the menstrual device 10, the fluid will initially collect to a middle region. As it collects in the middle region, fluid travels downwardly and outwardly from where the fluid is being directed into the menstrual device 10 as the frame 12 (absorbent layer 19, and/or absorbent article 18, as discussed below) absorbs fluid. As the frame 12 (absorbent layer 19, and/or absorbent article 18, as discussed below) absorbs fluid and meets its gram per gram capacity, the fluid is collected upwardly and outwardly. If the length of the cavity 26 (or cavities) exceeds 75% of the length of the menstrual device 10, the fluid will collect from the bottom region upward.

Fluid collection for a menstrual device 10 embodiment is exemplified by FIGS. 20A-20D, and is generated by micro-CT scanning using a radiotransparent test fixture applying a 0.25 psi pressure to simulate in-body pressures (note: the test fixture in FIGS. 20A-20D is dark grey, contrasted with menstrual device 10 seen as a lighter grey, and the fluid is seen as black, or darker than the text fixture and menstrual device 10). This test apparatus and methodology is described more fully in U.S. Patent Application Publication No. 2017/0135876 titled "Four-Dimensional Analysis System, Apparatus, and Method" which is incorporated by reference in its entirety. The menstrual device 10 is placed within a condom (or other fluid impermeable material/membrane; seen in FIGS. 20A-D in white surrounding menstrual device 10) with a line transmitting fluid placed directly above the proximal end 24 and centered over cavity 26 (the tip of the needle on the line is shown as the white moon-shaped feature at the top of each FIG. 20A-20D). Fluid is pumped at a controlled rate into the menstrual device 10 (shown in grey) over time ("t"), as demonstrated by FIGS. 20A-20D at exemplary times t=134 seconds, t=937 seconds, t=1205 seconds, and t=1370 seconds, respectively. As demonstrated by the figures, the middle region of the menstrual device 10 collects fluid, distributing fluid downward towards distal end 22, radially outward, and thereafter collects upward until the entire menstrual device volume is exhausted.

Figure 21A:
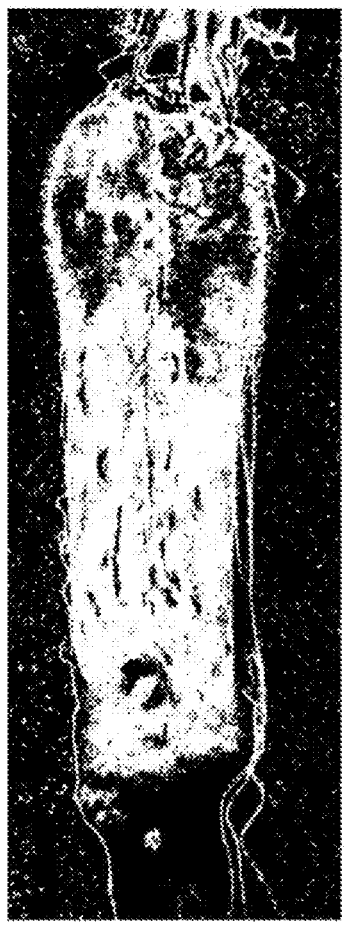
FIGS. 21A-C are radiographic images of a commercially available tampon pledget
Figure 21B:
Figure 21C:

FIGS. 21A-21C demonstrate how commercially available tampon pledgets absorb fluid, in the aforementioned test apparatus with the same set-up, having exemplary times t=55 seconds, t=110 seconds, and t=386 seconds, respectively. As shown, commercially available tampons absorb fluid top-down.

In any embodiment, the compact configuration dimensions are less than the aforementioned dimensions in the at-rest configuration. In any embodiment, the deployed configuration dimensions can be up to or equal to the aforementioned dimensions in the at-rest configuration. As discussed above, these dimensions take into account various parameters including typical length, depth and width of the vaginal canal, pressure exerted by the vaginal canal, collection capacity meeting or exceeding existing internally worn menstrual devices such as cups and tampons, and mitigating against leakage and vaginal irritation such as dryness caused by commercially available rayon/cotton tampon products.

The seal layer 28 is disposed on at least a portion of the exterior surface 34 of the side wall 20. In those embodiments wherein the frame 12 includes a distal end exterior surface 40, the seal layer 28 is also disposed on the distal end exterior surface 40.

In some embodiments, the seal layer 28 is disposed on only a portion of the exterior surface 34 of the side wall 20; i.e., the seal layer 28 extends from the distal end 22 toward, but not completely to, the proximal end 24; e.g., see FIGS. 1 and 1A. In some of these embodiments, the seal layer 28 is impermeable and as such, to increase the amount of surface area of the frame 12 that can collect fluid (and thus help mitigate against leakage), a portion of the frame 12 is not covered by the seal layer 28. In some embodiments, the length of the exterior surface 34 of side wall 20 that is not covered by the seal layer 28 is up to 75% of the total length of the menstrual device 10, or up to 50%, up to 35%, or greater than 10%. In some embodiments, the length of the exterior surface 34 of side wall 20 that is not covered by the seal layer 28 is between about 10% and about 35%.

In some embodiments, the seal layer 28 is disposed on the entirety of the exterior surface 34 of the side wall 20; i.e., the seal layer 28 extends from the distal end 22 all the way to the proximal end 24; e.g., see FIGS. 3A, 3B, 5A, and 5B. In some embodiments, the seal layer 28 is disposed on both the entirety of the exterior surface 34 of the side wall 20, and also covers at least a portion of the proximal end surface 36; e.g., see FIGS. 4A,4B, and FIG. 15A. In embodiments where the seal layer 28 is disposed on the proximal end surface 36, the seal layer 28 covers up to 50% of the proximal end surface, up to 35%, up to 25%, or up to 10%.

The seal layer 28 comprises one or more materials that collectively do not appreciably absorb fluid. In some embodiments, the seal layer 28 does not appreciably allow fluid to pass through the seal layer 28 and into the frame 12. For these embodiments, the seal layer 28 is a continuous, non-perforated layer that prevents the passage of fluid there through. Hence, the seal layer acts as a fluid barrier. As will be described below, in some embodiments the seal layer 28 may include perforations that allow a limited amount of fluid transfer across the seal layer 28 such that it may be stored, retained and collected in menstrual device 10, but mitigate against fluid travelling across the perforated seal layer and out of the menstrual device 10 (i.e. by capillary action). In some embodiments, seal layer 28 is hydrophobic.

The seal layer 28 may be comprised of a variety of different types of materials and is not therefore limited to any particular type of material provided such material(s) is capable of functioning as a fluid barrier. Examples of acceptable seal layer 28 materials include molded or thermoformed polymers, flexible films, hydrophobic nonwoven materials, nylon, silicone, polyacrylate, polyurethane, polypropylene, polyethylene and other inert olephins. Preferably any such material is provided in a form that is medical grade and/or biocompatible. Some exemplary films are those made by Bayer, Vancive or Bemis (i.e. Bemis ST-104, Bemis ST-804, Bayer VPT 9074). As will be described in more detail below, the seal layer 28 functioning as a fluid barrier (in particular those embodiments where the seal layer 28 provides a complete fluid barrier) provides several advantages. For example, because the seal layer 28 does not permit fluid transfer from a vaginal wall (i.e., the wall the device is in contact with) into the menstrual device 10, the seal layer 28 prevents the migration of menstrual fluids or other body fluids away from the vaginal wall. As a result, the menstrual device 10 is less apt to be associated with undesirable, potentially irritating, vaginal wall dryness. In this regard, it can be seen that the present menstrual device 10 does not function as a tampon typically functions. As another example, the seal layer 28 functioning as a fluid barrier also enables the frame 12 to collect and retain menstrual fluids; e.g., menstrual fluids collected within the interior cavity 26 of the menstrual device 10 are retained within the interior cavity 26. In those embodiments wherein the frame 12 comprises a foam material, the amount of menstrual fluid that can be collected is a function of the interior cavity volume as well as the porous void volume of the frame material. Current testing indicates that these menstrual device configurations can collect and hold up to four times (4×) the volume of menstrual fluid prior to leakage as compared with the maximum menstrual volume a typical tampon pledget can absorb prior to leakage. In addition, the length of time a typical tampon pledget can be worn is influenced by the volume of fluid it can absorb prior to leakage. The ability of the present menstrual device 10 to collect a substantially greater volume of fluid (up to 4×) prior to leakage, significantly increases the duration of time the menstrual device 10 can be comfortably worn without leakage.

Experimentation has been done to determine the volume capacity of various embodiments of the present disclosure. Testing has been performed with two different set-ups, using, on the one hand, a syngyna apparatus, and on the other, an Ion Simulator. The sygina apparatus used a 1% saline solution [as required by the FDA] and a flow rate of 0.8 ml/min, while the Ion Simulator used a synthetic menstrual fluid and a flow rate of 2 ml/min. below chart describes various embodiments demonstrating collection up to about four times a regular tampon (i.e. with an absorbency between 6 g and 9 g). The below chart describes the dry weight of the menstrual device versus the amount of fluid (in grams) the menstrual device can collect. Samples with 1.5" and 2" lengths were tested, having a 1.75" proximal end diameter. All embodiments tested have a seal layer including a biocompatible film.

As demonstrated in FIG. 23, varying the geometry of the menstrual device 10 has an effect on the g/g absorbency. The above indicates the menstrual device of the present disclosure has a g/g absorption when using the aforementioned syngyna set-up, exceeding 5 g/g, or between 5 g/g and 7 g/g. Using the aforementioned Ion Simulator methodology, the menstrual device of the present disclosure has a g/g absorption exceeding 8 g/g, between 8 g/g/ and 11 g/g. Also demonstrated in FIG. 23, the menstrual device 10 has an absorbent capacity of at least 15 g, or at least 18 g, or at least 22 g, as measured by the syngyna apparatus using a 1% saline solution and a flow rate of 0.8 ml/min.

As exemplified above, by comparing the two different test methodologies and fluids, on can more readily correlate absorbency information based on less viscous fluids (i.e. 1% saline) and more viscous fluids (the synthetic menstrual fluid). The correlation factor of typical syngyna fluid to synthetic menstrual fluid is about 0.6. This enables correlation between various set-ups and parameters (i.e. in vivo studies and in vitro studies).

The seal layer 28 may also improve the ease with which the menstrual device 10 is ejected from the applicator 52. Due to the menstrual device 10 having an at-rest, expanded configuration, ejecting menstrual device 10 from applicator 52 can be difficult for the user (i.e. requiring the exertion of a greater amount of force than with known tampons). The seal layer 28 is a smooth and/or slippery material such that its coefficient of friction is less than that of the frame 12 material. As such, seal layer 28, when applied to frame 12, can, in embodiments including an applicator 52, reduce the ejection force of the menstrual device 10 from applicator 52 to be less than 50 ounces, less than about 40 ounces, preferably less than 30 ounces and more preferably, less than or equal to about 20 ounces.

The seal layer 28 may be applied to the exterior surface 34 of the side wall 20 using a variety of different techniques (e.g., applied as a film, or as a coating applied by a spray process or a dipping process, etc. . . . ), and the seal layer 28 application process is not limited to any particular technique. Seal layer 28 materials may be adhered to the frame 12 using an adhesive. Seal layer 28 materials may alternatively be applied to the exterior surface 34 and subsequently subjected to a curing type process (e.g., elevated temperatures, UV light, etc.) that causes the seal layer 28 material to bond or otherwise adhere to the exterior surface 34. In those embodiments wherein the seal layer 28 material is formed as a film prior to application to the frame 12, the seal layer 28 film may be applied using a vacuum forming process. In some embodiments where a film seal layer 28 is used, the film seal layer 28 may include a plurality of film sublayers. For example, the film seal layer 28 may include a first sublayer comprised of a first thermoplastic material having a first melt temperature and a second sublayer comprised of a second thermoplastic material having a second melt temperature, wherein the second melt temperature is lower than the first melt temperature. In this embodiment, the film seal layer 28 is applied to the frame 12 such that the second sublayer is disposed in contact with the exterior surface 34 of the side wall 20 and the first sublayer is exposed; i.e., the second sublayer is disposed between the first sublayer and the side wall exterior surface 34. During the film seal layer 28 application process, the film seal layer 28 is subjected to a temperature at or above the melt temperature of the second sublayer, but below the melt temperature of the first sublayer. As a result, the second sublayer acts to bond the first sublayer to the frame 12.

As indicated above, in some embodiments the seal layer 28 as described above may include perforations that allow a limited amount of fluid transfer across the seal layer 28. The collective area of the perforations is substantially smaller than the area of the seal layer 28. Because the collective perforation area is much smaller than the entire seal layer area, the amount of fluid transfer across the seal layer 28, is minimal. Hence, a perforated seal layer 28 still predominantly functions as a fluid barrier. To the extent that there is fluid transfer across the seal layer 28 via the perforations, it is understood such fluid transfer is likely to be fluid transfer into the menstrual device 10.

Figure 10A:
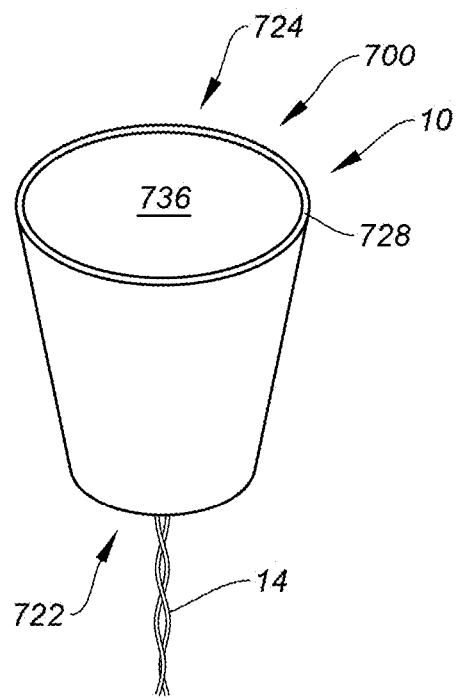
FIG. 10A is a diagrammatic angled view of a menstrual device embodiment according to the present disclosure.
Figure 10B:
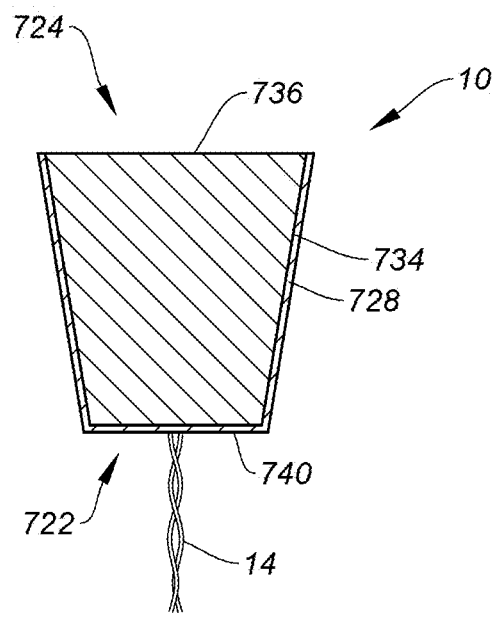
FIG. 10B is a diagrammatic lengthwise sectional view of the menstrual device embodiment shown in FIG. 10A.

In an alternative embodiment of the present disclosure shown in FIGS. 10A and 10B, the menstrual device 10 includes a body 700 defined by at least one side surface 734, a distal end 722, a proximal end 724, and a seal layer 728. The side surface 734 extends between the distal end 722 and the proximal end 724. The proximal end 724 has a proximal end surface 736. In this embodiment, the menstrual device 10 does not include an interior cavity. The distal end 722 may also have a distal end surface 740, depending on the specific geometry of the menstrual device 10.

Figure 11:
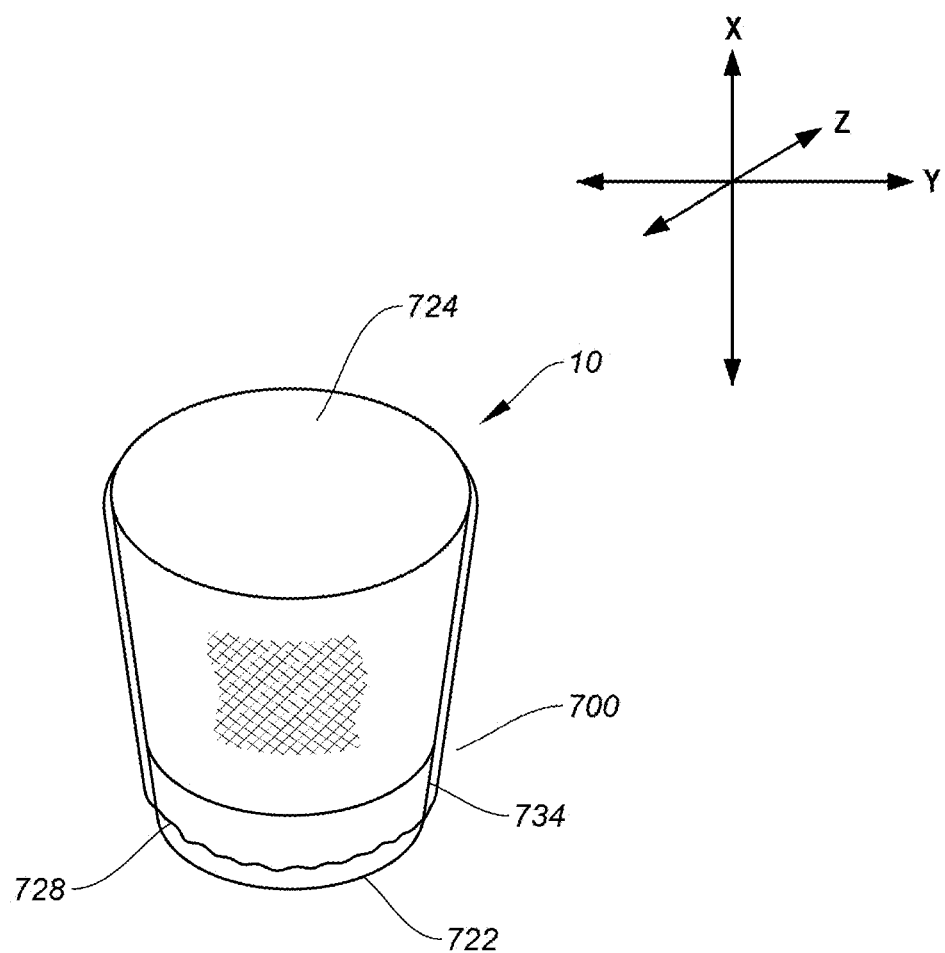
FIG. 11 is a diagrammatic angled view of a menstrual device according to the present disclosure.
Figure 12:
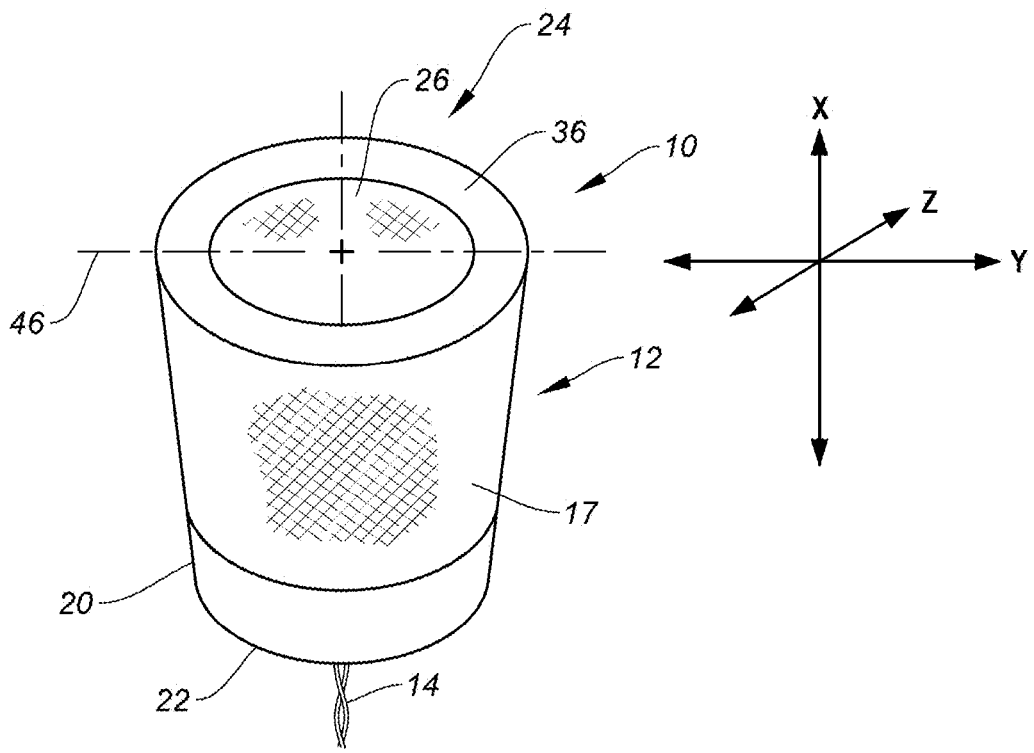
FIG. 12 is a diagrammatic angled view of a menstrual device embodiment according to the present disclosure.
Figure 12A:
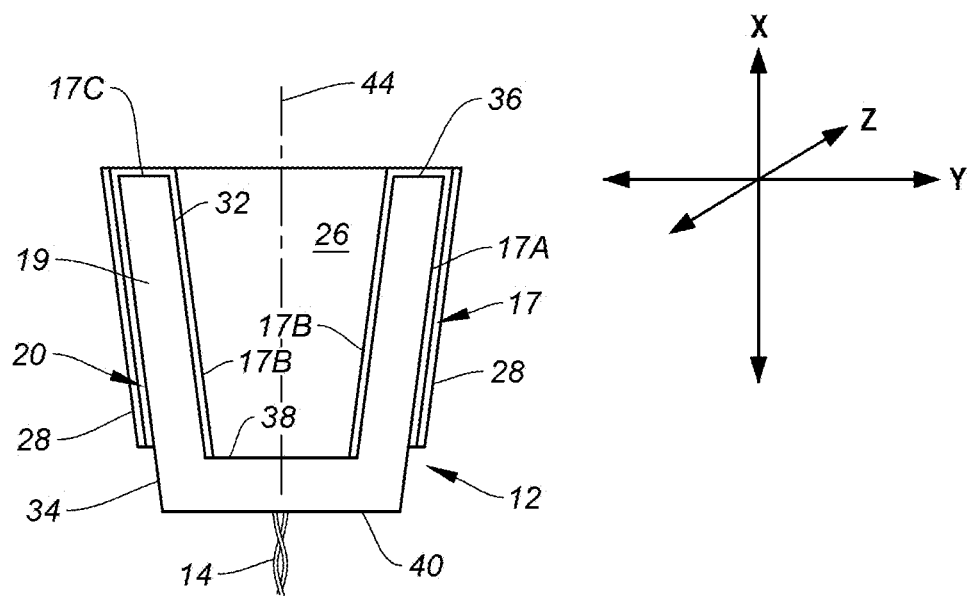
FIG. 12A is a diagrammatic lengthwise sectional view of a menstrual device embodiment like that shown in FIG. 12, illustrating a support element embodiment.
Figure 12B:
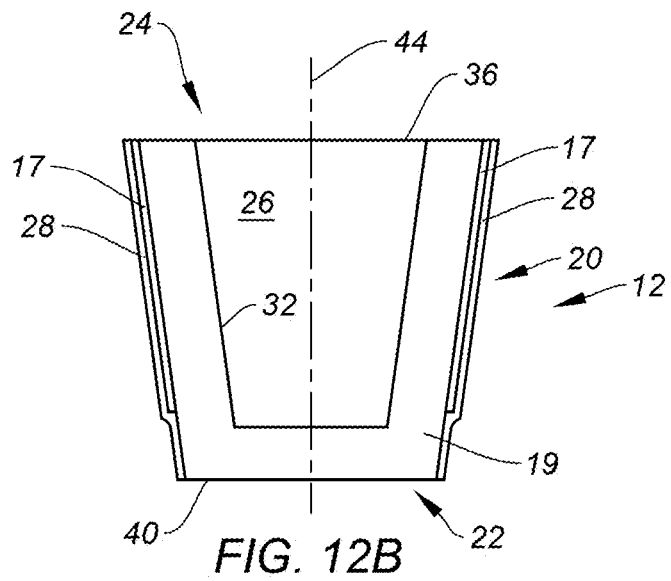
FIG. 12B is a diagrammatic lengthwise sectional view of a menstrual device embodiment like that shown in FIG. 12, illustrating a support element embodiment.
Figure 12C:
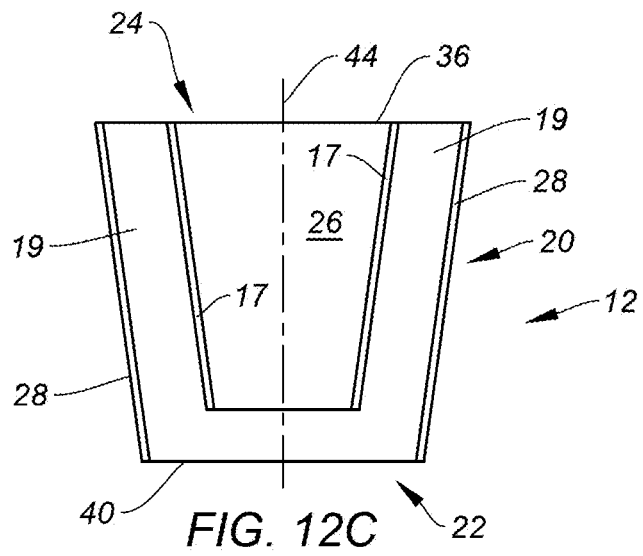
FIG. 12C is a diagrammatic lengthwise sectional view of a menstrual device embodiment like that shown in FIG. 12, illustrating a support element embodiment.
Figure 12D:
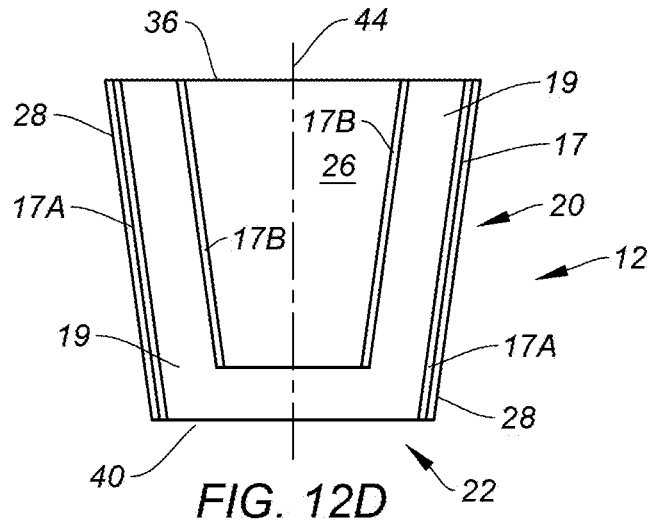
FIG. 12D is a diagrammatic lengthwise sectional view of a menstrual device embodiment like that shown in FIG. 12, illustrating a support element embodiment.

Referring to FIGS. 11 and 12-12D, embodiments of the present menstrual device 10 include a support element 17. The menstrual device 10 exemplified in FIG. 11, similar to FIGS. 10A and 10B, does not have an interior cavity. As shown in FIG. 11, the menstrual device 10 includes a body 700 defined by at least one side surface 734, a distal end 722, a proximal end 724, and a seal layer 728. The side surface 734 extends between the distal end 722 and the proximal end 724. The proximal end 724 has a proximal end surface 736. In this embodiment, the menstrual device 10 does not include an interior cavity.

In some embodiments, the frame 12 includes the support element 17 and an absorbent element 19. The frame is configured so it can be elastically deformed or folded into a compact configuration and can also be expanded into an expanded configuration, i.e., expanded into a deployed configuration or an at rest configuration.

In some embodiments, the support element 17 completely encompasses the absorbent element 19. The distal end 722 may also have a distal end surface, depending on the specific geometry of the menstrual device 10.

FIGS. 12-12D provide embodiments including an alternate collection means, having a support member 17, an absorbent element 19 that form a side wall 20, a distal end 22, a proximal end 24, an interior cavity 26, and a seal layer 28. Absorbent element 19 includes materials described throughout this application relating to frame 12. Seal layer 28 can be close-forming around support element 17 and/or absorbent element 19, or can be loose-fitting like a bag, thereby enabling the support element 17 and/or absorbent element 19 to be freely dynamic (i.e. expand upon fluid collection). For clarity, in embodiments where seal layer 28 is elastic such that support element 17 and/or absorbent element 19 are dynamic.

In some embodiments, the support element 17 is configured to elastically self-expand; e.g., if radially compressive forces less than those required to hold the support element 17 in a compact configuration are applied to the support element 17, the self-expanding support element 17 will radially expand into a deployed configuration, or if no radially compressive forces are applied to the support element 17, the self-expanding support element 17 will radially expand into an at rest configuration. In the at rest configuration, the self-expanding element assumes a predetermined geometric shape. The elastically self-expanding support element 17 expands without utilizing any liquid (absorbed or otherwise) as a mechanism of change. This type of support element 17 may be referred to as having an "elastic memory". In other embodiments, the support element 17 does not elastically self-expand, or is incapable by itself of causing the menstrual device to self-expand to a deployed configuration.

The support element 17 allows the passage of menstrual fluid through the support element 17, and therefore does not provide a fluid sealing function. For example, the support element 17 may be formed, at least in part, from one or more materials arranged as a mesh. In these embodiments, the support element 17 is not limited to any particular type of mesh arrangement provided the mesh can be elastically deformed or folded into a compact configuration and can also be expanded into an expanded configuration. Some examples include braided mesh. The support element 17 is not, however, limited to being formed as a mesh, or having one or more portions formed as a mesh. For example, the support element 17 may be formed in part from a woven material, a perforated material, or a non-porous or solid material, or the like, or combinations thereof.

The support element 17 is not limited to any particular type material, however medical grade and/or biocompatible materials are preferred. Non-limiting examples of materials that may be used to form a mesh support element 17 include any rigid or semi rigid materials, such as polyolefins (i.e. polypropylene, polyester, and polyethylene), thermoplastic elastomers, nylons, and silicones. In some embodiments, the mesh support element 17 is non-absorbent in its own right. In some embodiments, the mesh support element 17 assists in retention and storage of fluid within menstrual device 10. In some embodiments, the mesh support element assists in directing fluid into and/or within menstrual device 10.

The absorbent element 19 comprises a material operable to absorb menstrual fluids either physically or chemically, or some combination thereof. The absorbent element 19 is capable of being elastically deformed or folded into a compact configuration and can also be disposed into an expanded configuration; i.e., disposed in a deployed configuration or an at rest configuration.

In some embodiments, the absorbent element 19 is configured to elastically self-expand; e.g., if radially compressive forces less than those required to hold the absorbent element 19 in a compact configuration are applied to the absorbent element 19, the self-expanding absorbent element 19 will radially expand into a deployed configuration, or if no radially compressive forces are applied to the absorbent element 19, the self-expanding absorbent element 19 will radially expand into an at rest configuration. In the at rest configuration, the self-expanding absorbent element 19 assumes a predetermined geometric shape. The elastically self-expanding absorbent element 19 expands without utilizing any liquid (absorbed or otherwise) as a mechanism of change. This type of absorbent element 19 may be referred to as having an "elastic memory". In other embodiments, the absorbent element 19 does not elastically self-expand, or is incapable by itself of causing the menstrual device to self-expand to a deployed configuration.

For those embodiments where the absorbent element 19 is configured to elastically expand, an acceptable absorbent element material is an elastic polymer that can be formed into a geometric shape useful for a menstrual device 10; e.g., an elastic polymer formed to assume a desired geometric shape and volume in an at rest configuration (i.e., in the absence of applied forces) and which polymer can be elastically compressed to a smaller volume and thereby assume a reduced volume configuration (e.g., a deployed configuration or a compact configuration). Specific non-limiting examples of elastic polymers include medical grade and/or biocompatible polyester, polypropylene, or polyurethane foams. The term "foam" as used herein refers to a substrate construction having internal voids, which voids may vary in size and number per volumetric unit.

For those embodiments where the absorbent element 19 does not elastically self-expand, acceptable absorbent element materials include, but are not limited to, wood pulp, rayon, cotton, natural or synthetic nonwoven materials, super-absorbent materials (e.g., fibers, films, particles), nanocellulose materials, foams, or any combination thereof. The absorbent material(s) 16 is preferably medical grade and/or biocompatible.

As indicated above, embodiments of the present menstrual device 10 include a frame 12 having at least one side wall 20, a distal end 22, a proximal end 24, and an interior cavity 26, wherein the interior cavity 26 may be completely defined by the interior surface 32 of the side wall 20, or may be defined by the interior surface 32 of the side wall 20 and the interior surface 38 of the distal end 22. At least a part of the frame side wall 20 includes both the support element 17 and the absorbent element 19. In some embodiments (as can be seen in FIGS. 12-12D), the support element 17 is disposed radially outside of the absorbent element 19. The support element 17 may extend the entirety of the side wall (from proximal end to distal end; outside of the absorbent element 19, or less than the entirety. In some embodiments, the support element 17 is disposed radially inside of the absorbent element 19. For example, FIG. 12C shows an embodiment wherein the entirety of the support element 17 is disposed radially inside of the absorbent element 19. In any embodiment having at least a portion of the support element radially inside of the absorbent element 19, the support element 17 may extend the entirety of the side wall (from proximal end to distal end) radially inside of the absorbent element 19, or less than the entirety. In some embodiments (as can be seen in FIGS. 12A and 12D), the support element 17 may include a portion disposed radially outside of the absorbent element 19 and a portion disposed radially inside of the absorbent element 19. For example, the embodiment shown in FIG. 12D includes an outer support element portion 17A and an inner support element portion 17B, which portions are independent of one another. The embodiment shown in FIG. 12A includes an outer support element portion 17A and an inner support element portion 17B, and also includes a proximal end support element portion 17C that is connected to the other portions 17A, 17B. In other words, the support element 17 embodiment shown in FIG. 12A extends from a radially outer portion 17A (e.g., disposed on the interior surface 32 of the side wall 20), over the proximal end surface 36 (e.g., proximal end portion 17C), to a radially inner portion 17B (e.g., disposed on the exterior surface 34 of the side wall 20). The support element 17 may extend around the entire circumference of the menstrual device 10.

As described above, some embodiments of the present menstrual device include a frame 12 having a support element 17 that is configured to elastically self-expand. In some of these embodiments, it is the support element 17 that solely provides the radial expansion force (described below) adequate to cause the menstrual device 10 to elastically self-expand from a compact configuration to a deployed configuration or an at rest configuration. Also as described above, some embodiments of the present menstrual device include a frame 12 having an absorbent element 19 that is configured to elastically self-expand. In some of these embodiments, it is the absorbent element 19 that solely provides the radial expansion force adequate to cause the menstrual device 10 to elastically self-expand from a compact configuration to a deployed configuration or an at rest configuration. In still other embodiments of the present menstrual device 10, the support element 17 and the absorbent element 19 both provide radial expansion forces and thereby collectively provide the radial expansion forces necessary to cause the menstrual device 10 to elastically self-expand from a compact configuration to a deployed configuration or an at rest configuration.

The mechanical material properties of the frame material(s) that enable the frame 12 to elastically expand from a compact configuration to an expanded configuration may be described in terms of "expansion forces". To illustrate, consider a frame 12 maintained in a deployed configuration (i.e., wherein the menstrual device 10 assumes a volume less than the volume of the same device in an at rest configuration). Body wall surfaces 50 (i.e., vaginal wall surfaces) in contact with the menstrual device 10 prevent the menstrual device 10 from assuming its fully expanded configuration, and thereby maintain the menstrual device 10 in the partially compressed deployed configuration. As a result, the expansion forces 51 that would otherwise cause the menstrual device 10 to elastically expand to an at rest configuration, now act against the body wall surfaces 50. Those expansion forces 51, which are quantifiable, are at least a part of the mechanism that enables the menstrual device 10 to be maintained at a particular position within the user's vagina. It should be noted from the above that menstrual devices 10 according to the present disclosure are intended to assume an expanded configuration, albeit one that is partially compressed configuration (i.e. a deployed configuration), during in vivo use. The expansion forces 51 are described as being "at least part of the mechanism" that enables the device to be positionally retained because other factors may also play a part in retaining the device; e.g., the coefficient of friction of the exposed surface of the seal layer 28, the coefficient of friction of the body wall surface 50, the geometric shape of the menstrual device 10, etc. For the present menstrual device embodiments, the frame 12 is chosen to have mechanical material properties (as described above) that produce expansion forces adequate to retain the device 10 in vivo in a deployed configuration, while at the same time such expansion forces 51 are preferably below a magnitude that: a) would cause user discomfort; b) inhibit or prevent the menstrual device 10 from being placed in a compact configuration (e.g., for insertion purposes with or without an applicator); and/or c) inhibit removal of the menstrual device from in vivo deployment. The expansion forces 51 produced by the frame material are further discussed below in the context of an applicator device that may be used with the present menstrual device 10.

As shown in FIGS. 13-15A, the menstrual device further includes a flange 13 that further mitigates against leakage. Flange 13 provides a gasketing effect thereby assisting with creating a seal with the vaginal wall. Flange 13 is flexible such that it is configurable in a compact form (i.e. it can fold or scrunch). In some embodiments, flange 13 extends outwardly from exterior surface 34 of the menstrual device 10. In further embodiments, flange 13 extends outward and upward from the exterior surface 34 and proximal surface 36. In other embodiments, flange extends outward and downward from the exterior surface 34 and proximal surface 36. As flange 13 is flexible, it can be dynamic (i.e. move upward/downward, outward/inward) depending on placement within the vaginal wall and other factors such as the user's physical movement and/or the dynamic state of other organs/tissues. In some instances, flange 13 can actually create a dam and not only assist in collecting fluid within the menstrual device 10, but above the proximal surface 36.

Flange 13, as shown in FIGS. 8A-9B, and 14-15A, has multiple flanges 13A, 13B, and 13C. These additional flanges further assist in creating a seal with the vaginal wall, due to dynamic conditions experienced over time. Flanges are separated by grooves 15, 15A, 15B, and 15C. Flanges 13 and grooves 15 can be discrete from each other, continuous about the periphery of the menstrual device 10, and/or varied, patterned, etc. Flanges 13 are generally sized to extend outward widthwise or depthwise up to 0.5 inches, less than 0.35 inches, or between about 0.01 inches and about 0.3 inches. Flanges 13 are generally sized to extend in length along the lengthwise axis up to 0.5 inches, less than 0.35 inches, or between about 0.01 inches and about 0.3 inches. Grooves 15 have similar range of sizes.

As depicted in FIGS. 8A-9B, flanges 13 extend from frame 12. Seal layer 28 extends up to the inferior-most flange 13B. Although seal layer can extend and at least partially cover portions of a flange or flanges (or groove or grooves), it is preferred at least a portion of a flange (or flanges) is not covered by seal layer 28 such that, depending on how the menstrual device 10 is positioned within the vaginal canal, it enables further fluid collection through the permeable frame 12. As depicted in FIGS. 13-15A, flanges extends from support element 17. In embodiments where the seal layer 28 is the supper element 17, the flange 13 (or flanges) extends from the seal layer 28/support element 17.

Figure 13:
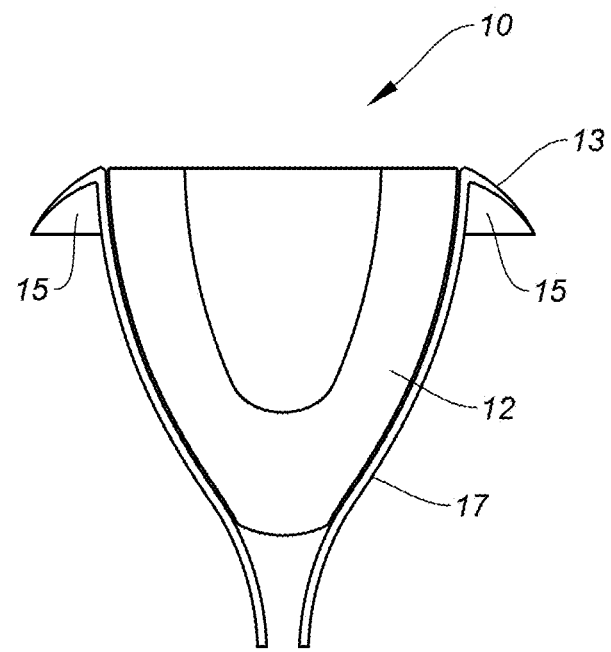
FIG. 13 is a diagrammatic lengthwise sectional view of a menstrual device embodiment according to the present disclosure.
Figure 14:
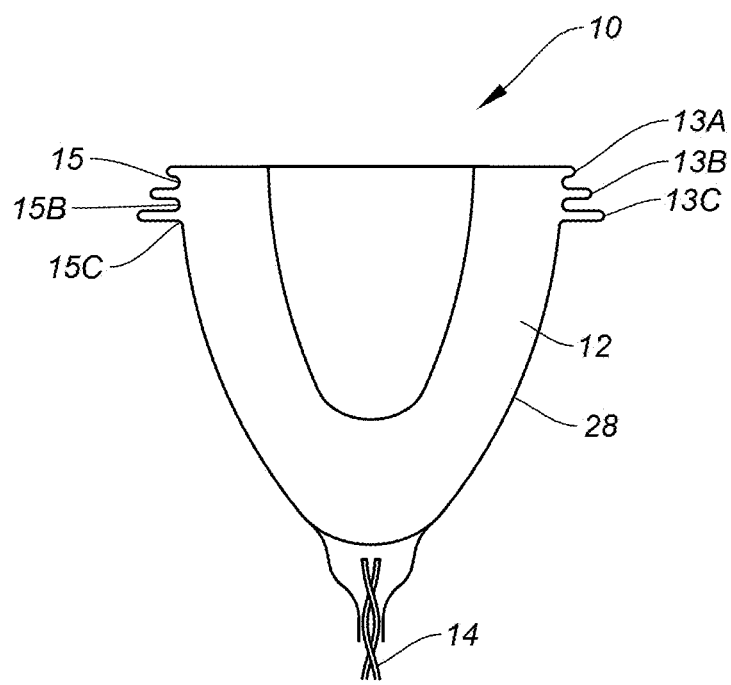
FIG. 14 is a diagrammatic lengthwise sectional view of a menstrual device embodiment according to the present disclosure.
Figure 15:
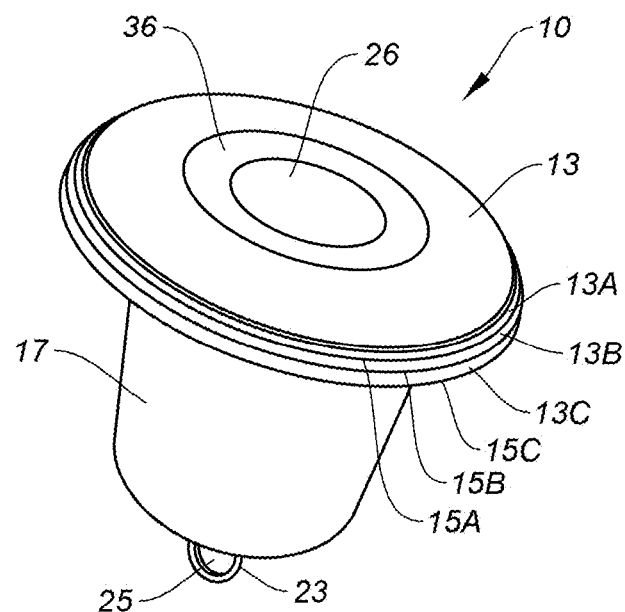
FIG. 15 is a diagrammatic angled view of a menstrual device embodiment according to the present disclosure.
Figure 15A:
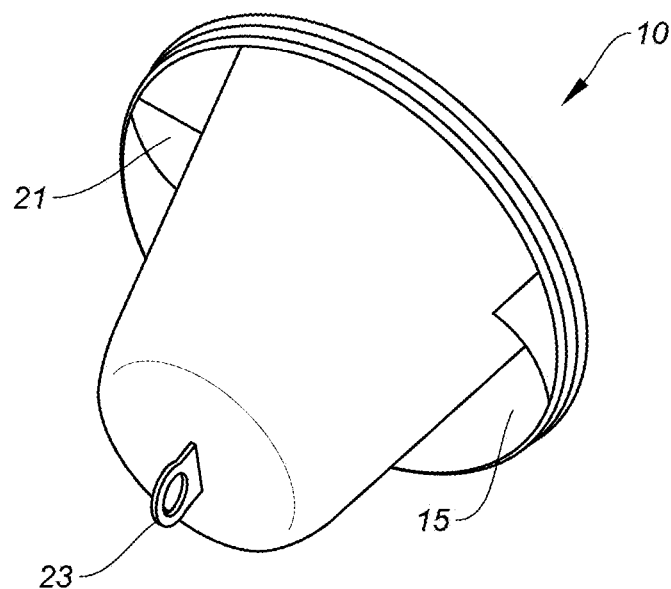
FIG. 15A is a diagrammatic angled view of a menstrual device embodiment according to the present disclosure.

As shown in FIGS. 13 and 15A, the menstrual device 10 includes flange 15 in the form of a pocket or gusset. Optionally, one or more support ribs 21 (as shown in FIG. 15A) provide added resilience to flange 13 to mitigate against bypass leakage (by improving the seal created with the vaginal wall).

The support element 17 and the absorbent element 19 may be attached to one another directly or indirectly. Non-limiting examples of acceptable attachment mechanisms include adhesive, mechanical fasteners, bonding, etc. An example of an indirect attachment mechanism includes both the support element 17 and the absorbent element 19 being attached to the removal element 14, but not directly to each other.

The seal layer 28 is disposed on at least a portion of the exterior of the menstrual device 10. In those embodiments where the support element 17 is disposed radially outside of the absorbent element 19, the seal layer 28 may be disposed radially outside of the support element 17 (e.g., see FIGS. 12A, 12B, and 12D). In these embodiments, the seal layer 28 may be disposed on the entirety of the exterior surface of the support element 17, or on less than the entirety of the support element 17. In those embodiments wherein the support element 17 extends less than the entire distance between the proximal end and the distal end of the menstrual device, the seal layer may also be disposed on a portion of the exterior surface 34 of the side wall 20. In those embodiments wherein the support element 17 is only disposed radially inside of the absorbent element 19, the seal layer 28 may be disposed on the entirety of the exterior surface 34 of the side wall 20 (e.g., the entire distance between the proximal end and the distal end, and contiguous with the absorbent element 19; see FIG. 12C), or less than the entirety of the exterior surface 34 of the side wall 20. In some embodiments, the seal layer 28 may cover at least a portion of the proximal end surface 36. In those embodiments wherein the frame 12 includes a distal end exterior surface 40, the seal layer 28 may also be disposed on the distal end exterior surface 40.

The removal element 14 is typically disposed at the distal end 22 of the menstrual device 10 and is configured to facilitate removal of the menstrual device 10 from the user's vagina. The removal element 14 may be a component independent of the frame 12 or seal layer 28, but attached to one or both of the frame 12 and seal layer 28. An acceptable example of an independent removal element 14 is a string. The use of strings as a menstrual device 10 (e.g., a tampon or menstrual cup) is well known in the art, and therefore further description is not provided herein. In some embodiments, the removal element 14 may be incorporated into the frame 12 or seal layer 28; an extension of the frame 12 or the seal layer 28, or some combination thereof.

The removal element 14 is typically disposed at the distal end 22 of the menstrual device 10 and is configured to facilitate removal of the menstrual device 10 from the user's vagina. The removal element 14 may be a component independent of the frame 12 or seal layer 28, but attached to one or both of the frame 12 and seal layer 28. In regards to the removal element 14 being attached to the frame 12, the removal element 14 may be attached to one or both of the support element 17 and the absorbent element 19. An acceptable example of an independent removal element 14 is a string. The use of strings as a menstrual device 10 (e.g., a tampon or menstrual cup) is well known in the art, and therefore further description is not provided herein. In some embodiments, the removal element 14 may be incorporated into the frame 12 or seal layer 28; an extension of the frame 12 or the seal layer 28, or some combination thereof.

In some embodiments, the seal layer 28 can be folded over itself and sealed to itself (in its entirety or minimally at the end points 31 of the fold(s) 33 to provide multiple layers in the seal layer 28. End points 31 are a single node or describe a peripheral end point for attachment. One skilled in the art understands that in any embodiment having a seal layer 28, end points 31 are minimally included (i.e., an upper end point that is discrete or peripheral, and a lower end point that is discrete or peripheral). This is advantageous in that it provides redundancy in impermeability, particularly at the distal end 22, and it also improves the strength of seal layer. The seal layer strength is further advantageous when positioned in the bottom region of the menstrual device and can ultimately become the removal element in its entirety. In some embodiments, a further removal element (i.e. a string, coated string, braided string) can be attached to the folded seal layer 28. The folded seal layer at least about the bottom region (or in some embodiments, merely the distal exterior surface 40) provides added strength as it distributes what is typically a tensile load on the removal element 14 with through shear.

Figure 17:
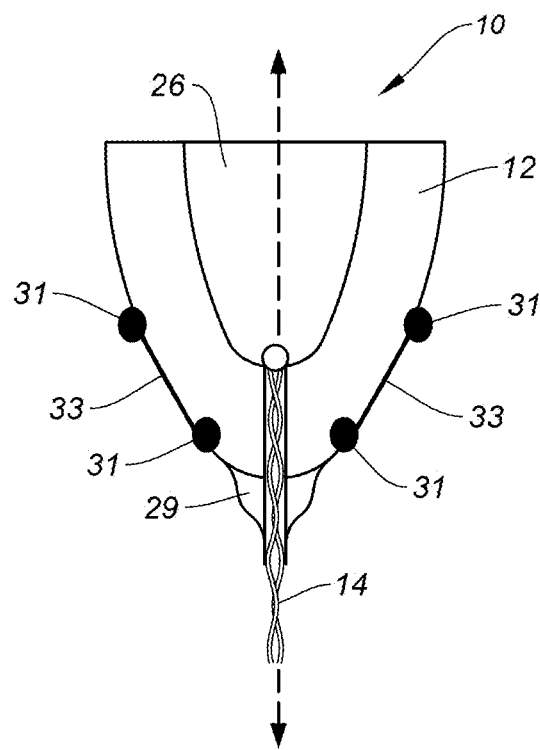
FIG. 17 is a diagrammatic side view of a menstrual device embodiment according to the present disclosure, where the dashed lines represent the lengthwise axis.

As shown in the embodiment in FIG. 17, seal layer 28 extends beyond the distal end 22. In such embodiments, seal layer 28 provides covering over a removal element 14, can be used to fasten the removal element 14 to the menstrual device 10, and/or be sealed to form a further fluid collection reservoir 29.

Figure 16:
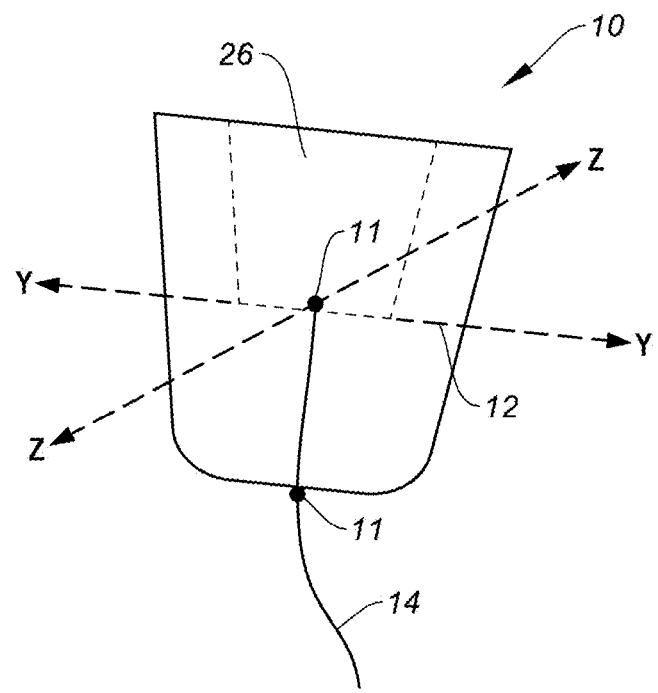
FIG. 16 is a diagrammatic side view of a menstrual device embodiment according to the present disclosure, where the dashed lines represent axes and internal features.

In other embodiments, the seal layer 28 and/or support layer 17 extend to form a ring 23 with hole 25, as shown in FIG. 15A. A removal element 14 can be fastened to the ring via a knot 11. In alternate embodiments, as shown in FIGS. 16-17, a removal element 14 is stitched or otherwise attached to the menstrual device. 10. Removal element 10 is attached via one or more knots, and can be attached along the lengthwise axis (as shown in FIG. 17), and/or can be attached just above either a step-change 17 in the cavity 26 and/or just above the bottom of the cavity 26. Attaching the removal element 14 as such improves the tensile strength.

All embodiments as contemplated in the present disclosure of the removal element 14 have been tested and meet the FDA's tampon requirements for having a tensile strength of at least eight pounds (i.e. stitched, knotted in the cavity, applied to the menstrual device by biocompatible adhesive, and/or tied to ring 25).

In some embodiments of the present disclosure, the menstrual device 10 may include a second absorbent element 18 (independent of the absorbent element 19) disposed within the interior cavity 26 of the frame 12 (e.g., see FIG. 6A). An example of a second absorbent element 18 is a tampon pledget, and can include materials such as rayon (multilobal, single lobal, cotton and/or combinations thereof). Tampon pledgets are well known in the art and the present menstrual device 10 is not limited to including any particular type of tampon pledget (i.e. including those with or without coverstock, formed wadded material and/or including discrete layers or pads). The second absorbent element 18 may be coupled to the frame 12 using one or more techniques; e.g., by adhesive, ultrasonic bonding, stitching, mechanical features, etc.

In some embodiments, menstrual device 10 includes a support element 17 and either absorbent layer 19 or second absorbent element 18. In some embodiments, the support element 17 is elastic and as the absorbent (element 18 or layer 19) absorbs fluid, the support element 17 expands. In such embodiments, support element helps create a seal and thus mitigates against bypass leakage.

In some embodiments of the present disclosure, the menstrual device 10 may include an absorbent article 18 disposed within the interior cavity 26 of the frame 12 (e.g., see FIGS. 5A and 5B). An example of an absorbent article 18 is a tampon pledget. Tampon pledgets are well known in the art and the present menstrual device 10 is not limited to including any particular type of tampon pledget. The absorbent article 18 may be coupled to the frame 12 using one or more techniques; e.g., by adhesive, ultrasonic bonding, stitching, mechanical features, etc.

In addition to, or as an alternative to the absorbent article 18, the menstrual device 10 may include one or more absorbent materials 16 disposed within the interior cavity 26; e.g., disposed on at least part of the interior surface 32 of the frame side wall 20 defining the interior cavity 26 (e.g., see FIGS. 4A and 4B) The absorbent material(s) 16 may comprise one or more material types; e.g., wood pulp, rayon, cotton, natural or synthetic nonwoven materials, superabsorbent materials (e.g., fibers, films, particles), nanocellulose materials, foams, or any combination thereof. The absorbent material(s) 16 is preferably medical grade and/or biocompatible.

Figure 19:
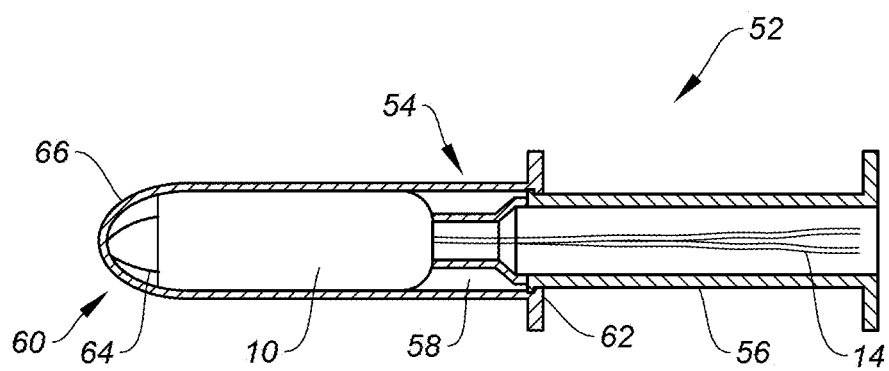
FIG. 19 is a diagrammatic view of system having an applicator and menstrual device according to the present disclosure.
Figure 20A:
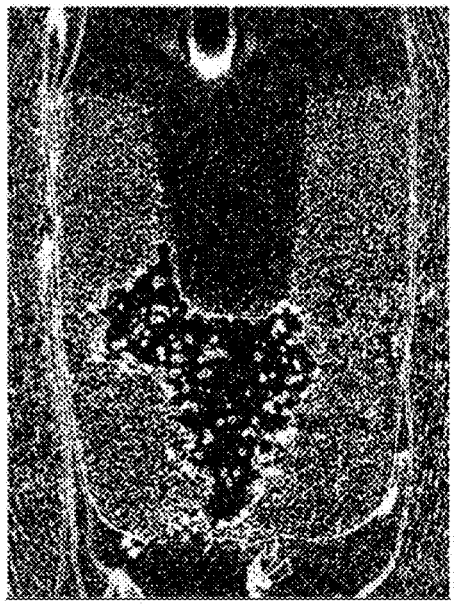
FIGS. 20A-D are radiographic images of a menstrual device according to the present disclosure.
Figure 20B:
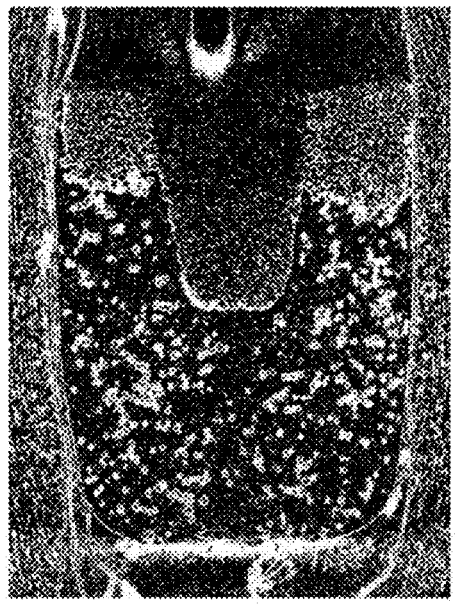
Figure 20C:
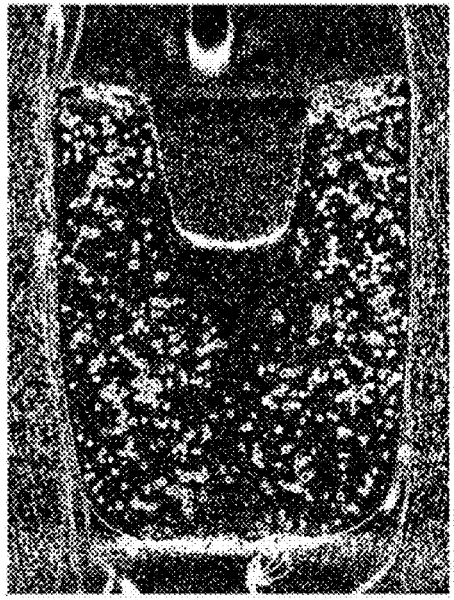
Figure 20D:
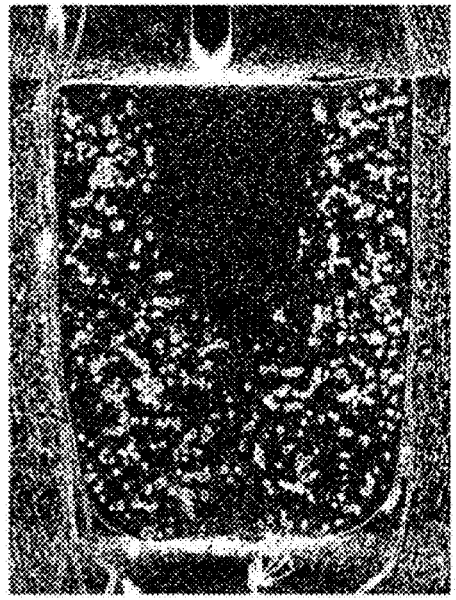

Now referring to FIG. 19, in some instances the present menstrual device 10 may be configured for use with an applicator 52 that facilitates deployment of the menstrual device 10 within the user's vagina. The combination of applicator 52 and menstrual device 10 may be referred to herein as a menstrual device system. Although the present menstrual device 10 is not limited to use with any particular type of applicator 52, an example of an acceptable type applicator 52 is a plunger type applicator having a barrel 54 and a plunger 56. The barrel 54 has a tubular configuration with an interior cavity 58 extending between an insertion tip end 60 and a plunger end 62. The insertion tip end 60 may have a plurality of slits 64 that form petals 66 that normally assume a radially inward geometry to give the insertion end a tapered configuration. The plunger 56 is receivable within the barrel interior cavity 58 and has a mating geometry relative to the barrel interior cavity 26 such at least a portion of the plunger 56 can be inserted into the barrel interior cavity 26; i.e., the plunger 56 can be moved axially into the barrel interior cavity 26. A menstrual device 10 disposed in a compact configuration can be disposed within the barrel interior cavity 26. Axial insertion of the plunger 56 into the barrel interior cavity 26 will axially move the menstrual device 10 against the petals 66. Continued axial insertion of the plunger 56 will cause the petals 66 to deflect radially outward and the menstrual device 10 to eject from the barrel 54.

The "Ejection Force" is described as the force required to eject a menstrual device 10 from the applicator. The Ejection Force can be determined using a scale such as a Tronix scale model #WI-130, and an Instron model 5944 with a 100 N load cell, using a rate of 12 in/min, and by following this procedure. All menstrual device 10 samples tested had a small amount of lubricant (K-Y True Feel Silicone Lubricant) applied to their periphery before being loaded into the applicators, as discussed below. The amount of lubricant included was minimal, such that upon ejection, no lubricant was noticeable by touch.

Procedure: Ejection Force
1. Zero out the scale and ensure it is weighing in ounces (other units of Force are also acceptable, such as Newtons).
2. Grasp the applicator (containing a tampon) by the finger grip using the thumb and index finger. Place the applicator, plunger end down, on top of the balance platform. Apply a steady downward motion until the menstrual device is ejected from the barrel. Apply the least amount of pressure possible, while ejecting the menstrual device from the barrel.
3. Record the maximum Ejection Force indicated by the scale (Note: the Ejection Force is recorded automatically if the scale is used in conjunction with computer running data collection software).

In those embodiments wherein the present menstrual device 10 is intended to be used with an applicator 52 (e.g., the same as or similar to the applicator described above), the frame material(s) is chosen to have mechanical material properties that produce expansion forces below which the menstrual device 10 is detrimentally inhibited from being ejected from the applicator 52; i.e., the frame material expansion forces do not bind the menstrual device 10 within the applicator barrel 54. In such embodiments, the seal layer 28 material properties (e.g., surface finish) and the applicator barrel 54 material properties (e.g., surface finish) may be chosen to complement each other to facilitate ejection of the menstrual device 10 from the applicator barrel 54. For instance, the seal layer 28 is a smooth and/or slippery material such that its coefficient of friction is less than that of the frame 12 material. As such, seal layer 28, when applied to frame 12, can, in embodiments including an applicator 52, reduce the ejection force of the menstrual device 10 from applicator 52 to be less than 50 ounces, less than about 40 ounces, preferably less than 30 ounces and more preferably, less than or equal to about 20 ounces.

As shown below in FIG. 24, applicators used to confirm ejection force values included the PLAYTEX GENTLE GLIDE ultra, having an inside barrel diameter of 15.77 mm, the PLAYTEX SPORT super plus, having an insider barrel diameter of 14.34 mm, and the KIMBERLY CLARK POISE IMPRESSA applicator, having an insider barrel diameter of 19.03 mm. In short, applicators having an inside barrel diameter of between about 14 mm and about 20 mm are suitable for the menstrual device 10 of the present disclosure, or between about 14.25 mm and about 19.5 mm, or between 15 mm and about 19 mm. Various sizes of menstrual device 10 were used, including those with lengths of 1.5" and 1.75", having proximal end widths of 1.5" and 1.75", a cavity length of 0.25", 0.50" and 0.75 inches, with a maximum cavity radius at the proximal end of 0.75", 1" and 1.08". If not otherwise specified, the samples included a seal layer 28 made from a biocompatible film. At least five samples of each embodiment of the menstrual device 10 were tested.

Figure 18:
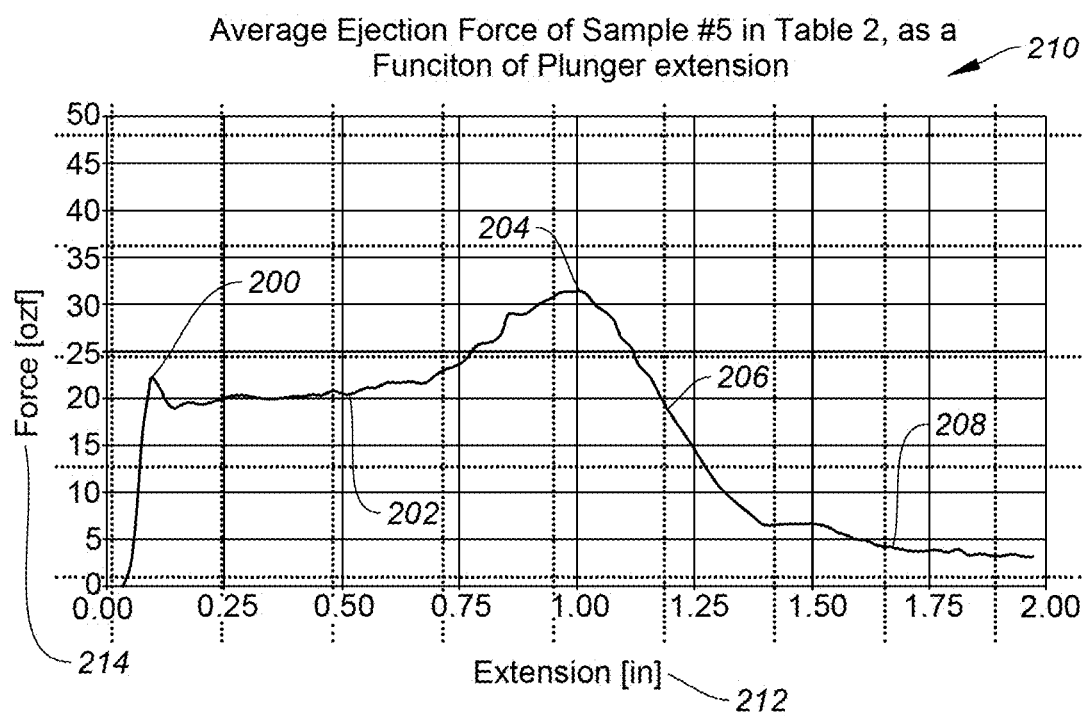
FIG. 18 is a chart describing the ejection force during the ejection process of a menstrual device embodiment according to the present disclosure.

As shown in the embodiment in FIG. 18, the ejection force changes during the ejection process, or as a function of time or length (note: length and time are related due to the 12 in/min rate, and the length of the stroke correlates to the length of the plunger moving against the menstrual device). FIG. 18 (reference numeral 210) describes various stages of ejection, starting with the plunger 56 initially contacting and depressing the menstrual device 10 at a force that exceeds that of the friction between the exterior surface of the menstrual device 10 and the interior surface of cavity 58 of the applicator 52 barrel 54 (see reference numeral 200). The vertical axis 214 describes ejection force in ounces, while the horizontal axis 212 describes extension of the plunger in inches. Once the force exerted by the plunger 56 exceeds this static friction force, the ejection force drops slightly as the menstrual device 10 begins sliding through the applicator barrel 54 prior to making contact with and opening the insertion tip end 60 of the applicator (see reference numeral 202). As the menstrual device 10 approaches the insertion tip end 60 and begins to apply pressure against the insertion tip end 60, the force increases until the insertion tip end 60 has been opened (see reference numeral 204). Once the insertion tip end 60 is opened, the menstrual device 10 starts to eject from the applicator at a reduced force (i.e. "self-ejection"; see reference numeral 206). Lastly, as shown by reference numeral 208, the menstrual device 10 goes through the final stages of ejection at a low level of force.

The menstrual device 10 has numerous distinct ejection characteristics, including the ability to self-eject from the applicator 52 after the plunger 56 has moved at least about an inch. The plunger's 56 movement of at least about an inch has fully opened the applicator insertion tip 60. The plunger's 56 movement of at least about an inch has engaged the menstrual device 10 such that a substantial portion of the menstrual device 10 has been pushed beyond the applicator 52 insertion tip end 60.

Various embodiments of the menstrual device 10 of the present disclosure include various features. For instance, menstrual device 10 has a frame 12 which is optionally a support member 17 and absorbent material (18 or 19). A single material can act as either or both of a support member 17 and a seal layer 28, and in further embodiments, provides all or a portion of removal element 14.

While some of the examples described herein related to uses of a device configured to be deployed within a body cavity, aspects of the disclosure may be applied in other types of environments where fluid sealing, absorption, or collection may be needed; e.g., incontinence devices, etc.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope thereof. Therefore, it is intended that the present disclosure not be limited to the particular embodiment(s) disclosed as the best mode contemplated, but that the disclosure will include all embodiments falling within the scope of the present disclosure.

What is claimed is:

1. A menstrual device comprising:
    a frame having a side wall with an exterior surface and an interior surface, the side wall extends between a proximal end and a distal end, and the interior surface at least in part defines an interior cavity; and
    a fluid barrier seal layer disposed on the exterior surface of the side wall, the fluid barrier seal layer attached directly to the exterior surface about at least a first and an interior surface end point;
    wherein the menstrual device collects fluid,
    wherein the menstrual device has a device length defined by a central vertical axis between the proximal end and the distal end,
    wherein the menstrual device is configurable in a compact configuration and in an expanded configuration, and in the expanded configuration the interior cavity has a volume greater than zero
    wherein the frame has a length of between about 1.5 inches and about 2.0 inches,
    wherein the cavity has a diameter of greater than 0 inches and up to about 1.08 inches, and wherein the menstrual device has a length ratio defined as a length of the cavity divided by the length of the frame, wherein the length ratio is less than or equal to 1:2, and
    wherein the cavity comprises at least two cavities.

2. The menstrual device according to claim 1, wherein the distal end has an interior surface and the interior cavity is defined by the interior surface of the side wall and the interior surface of the distal end.

3. The menstrual device according to claim 2, wherein the fluid barrier seal layer is disposed on all of the exterior surface of the side wall.

4. The menstrual device of claim 3, wherein the proximal end includes a proximal end surface, and the fluid barrier seal layer is disposed on at least a part of the proximal end surface.

5. The menstrual device of claim 1, wherein the fluid barrier seal layer comprises at least one of a molded or thermoformed polymer, a flexible film, or a hydrophobic nonwoven material.

6. The menstrual device of claim 1, wherein the frame has a gram per gram absorbency of greater than or equal to 5 g/g as measured by a syngyna apparatus using a 1% saline solution and a flow rate of 0.8 ml/min.

7. The menstrual device of claim 1, wherein the fluid barrier seal layer attaches to a withdrawal element.

8. The menstrual device of claim 1, wherein the frame comprises a support element and an absorbent element.

9. The menstrual device of claim 8, wherein the absorbent element is a layer or a tampon.

10. The menstrual device of claim 8, wherein at least one of the support element or the absorbent element is configured to elastically self-expand, and thereby cause the menstrual device to radially expand from the compact configuration to the expanded configuration in the absence of radially compressive forces.

11. The menstrual device according to claim 8, wherein the support element includes a silicone material.

12. The menstrual device according to claim 1, further comprising at least one flange extending outward from the proximal end.

13. A menstrual device comprising:
a frame having a side wall with an exterior surface and an interior surface, the side wall extends between a proximal end and a distal end, the interior surface at least in part defines an interior cavity; and
a fluid barrier seal layer disposed on the exterior surface of the side wall and is directly attached to the frame at least at a first point of attachment;
wherein the menstrual device collects fluid, and
wherein the menstrual device is configurable in a deployed configuration and in an at-rest configuration, the deployed configuration having a deployed footprint and the at-rest configuration having an at-rest footprint,
wherein the deployed footprint that is up to or equal to 100% of the at-rest footprint, and
wherein the menstrual device has a ratio of an exposed surface area of the cavity to the surface area of just the proximal end of between about 2.5 to 1 and about 1 to 1.

14. The menstrual device according to claim 13, wherein the fluid barrier seal layer is disposed on all of the exterior surface of the side wall.

15. The menstrual device according to claim 13, wherein the proximal end includes a proximal end surface, and the fluid barrier seal layer is disposed on at least a part of the proximal end surface.

16. The menstrual device according to claim 13, wherein the fluid barrier seal layer comprises at least one of a molded or thermoformed polymer, a flexible film, or a hydrophobic nonwoven material.

17. The menstrual device according to claim 13, wherein the fluid barrier seal layer attaches to a withdrawal element.

18. The menstrual device according to claim 13, wherein the frame comprises a support element and an absorbent element.

19. The menstrual device according to claim 18, wherein the support element includes a silicone material.

20. The menstrual device according to claim 13, further comprising at least one flange extending outward from the proximal end.

* * * * *